US009657302B2

(12) United States Patent
Daniell

(10) Patent No.: US 9,657,302 B2
(45) Date of Patent: May 23, 2017

(54) EXPRESSION OF HUMAN INTERFERON IN TRANSGENIC CHLOROPLASTS

(71) Applicant: The Trustees of the University of Pennsylvania, Philadelphia, PA (US)

(72) Inventor: Henry Daniell, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/537,661

(22) Filed: Nov. 10, 2014

(65) Prior Publication Data

US 2015/0361439 A1 Dec. 17, 2015

Related U.S. Application Data

(63) Continuation of application No. 10/520,104, filed as application No. PCT/US03/20869 on Jul. 2, 2003, now abandoned, said application No. 10/520,104 is a continuation-in-part of application No. 09/807,742, filed as application No. PCT/US01/06288 on Feb. 28, 2001, now abandoned, and a continuation-in-part of application No. 09/079,640, filed on May 15, 1998, now Pat. No. 7,129,391.

(60) Provisional application No. 60/393,438, filed on Jul. 3, 2002, provisional application No. 60/185,987, filed on Mar. 1, 2000, provisional application No. 60/263,473, filed on Jan. 23, 2001, provisional application No. 60/263,668, filed on Jan. 23, 2001.

(51) Int. Cl.
*C12N 15/82* (2006.01)
*C07K 14/56* (2006.01)

(52) U.S. Cl.
CPC .......... *C12N 15/8214* (2013.01); *C07K 14/56* (2013.01); *C12N 15/8257* (2013.01)

(58) Field of Classification Search
None
See application file for complete search history.

(56) References Cited

U.S. PATENT DOCUMENTS 4,616,078 A 10/1986 DiMarchi
4,956,282 A 9/1990 Goodman et al.
4,963,665 A 10/1990 Rotwein et al.
5,460,956 A * 10/1995 Reichert ................ C07K 14/56 424/85.7
5,693,507 A 12/1997 Daniell
5,792,640 A * 8/1998 Chandrasegaran ...... C12N 9/22 435/199
5,877,402 A * 3/1999 Maliga ............... C12N 15/8214 435/320.1
5,932,479 A 8/1999 Daniell
6,004,782 A 12/1999 Daniell et al.
6,642,053 B1 11/2003 Daniell
6,680,426 B2 1/2004 Daniell
7,129,391 B1 10/2006 Daniell
7,135,620 B2 11/2006 Daniell
7,294,506 B2 11/2007 Daniell
7,795,497 B2 * 9/2010 Daniell ................ C12N 9/0008 800/278
2002/0053094 A1 * 5/2002 McBride ................ C07K 14/61 800/278
2002/0162135 A1 10/2002 Daniell
2004/0177402 A1 9/2004 Daniell
2005/0108792 A1 5/2005 Daniell
2007/0124830 A1 5/2007 Daniell
2008/0241916 A1 10/2008 Daniell

FOREIGN PATENT DOCUMENTS

WO WO 98/56923 * 12/1998
WO 9910513 3/1999
WO 9910531 3/1999
WO WO 99/10513 * 3/1999
WO 9905265 4/1999
WO 9910513 4/1999
WO 9918225 4/1999
WO 0003012 1/2000
WO 0172959 4/2001

(Continued)

OTHER PUBLICATIONS

Aycock et al (1998, Crop Science 38:904).*
Baron et al., The interferons: mechanism of action and clinical applications, J. Amer. Med. Assoc, 1991, 1375-1383, 266.
Bogorad et al., Engineering chloroplasts: an alternative site for foreign gene, proteins, reactions and products, TIBTECH, 2000, 257-263,18.
Brixey et al., The chloroplast psbA promoter is more efficient in *E. coli* than the T7 promoter for hyper-expression of a foreign protein, Biotechnology Letters, 1997, 395-400, 19.
Carlson, P.S., The use of protoplasts for genetic research, Proc. Natl. Acad. Sci. USA, 1973, 598-602, 70.
Daniell et al., Medical molecular farming: production of antibodies, biopharmaceuticals and edible vaccines in plants, Trends Plant Sci., 2001a, 219-26, 6(5).

(Continued)

*Primary Examiner* — Anne Kubelik
(74) *Attorney, Agent, or Firm* — Kathleen D. Rigaut; Dann, Dorfman, Herrell and Skillman

(57) ABSTRACT

A plastid transformation vector for a stably transforming a plastid genome is provided. The vector includes, as operably-linked components, a first flanking sequence, a DNA sequence coding for a therapeutic human IFN, which is capable of expression in the plastid and a second flanking sequence. The invention also provides isolated and purified IFN, wherein the IFN is configured in a monomeric or multimeric form and is a structural equivalent to orally administered human IFN. Also provided are methods for variable-expressing biopharmaceutical proteins in plants suitable for mammal consumption. The method includes integrating a plastid transformation vector into a plastid genome of a plant cell; growing the plant cell to express a biopharmaceutical protein, such as therapeutic human interferon IFN. Also disclosed are plants transformed with the aforementioned vectors, and the progeny thereof. Also, disclosed is the IFN, which is IFNα2b.

9 Claims, 11 Drawing Sheets

(56) References Cited

FOREIGN PATENT DOCUMENTS

| | | |
|---|---|---|
| WO | 0164023 | 7/2001 |
| WO | 0164850 | 9/2001 |
| WO | 0164927 | 9/2001 |
| WO | 0164929 | 9/2001 |
| WO | 0172959 | 10/2001 |
| WO | 03057834 | 7/2003 |
| WO | 2004005467 | 1/2004 |
| WO | 2004005480 | 1/2004 |
| WO | 2004005521 | 1/2004 |
| WO | 2007053183 | 10/2007 |

OTHER PUBLICATIONS

Daniell et al., Expression of the native cholera toxin B subunit gene and assembly of functional oligomers in transgenic tobacco chloroplasts, Journal of Molecular Biology, 2001b, 1001-1009, 311.

Daniell et al., Marker free transgenic plants: engineering the chloroplast genome without the use of antibiotic selection, Curr Genet., 2001c, 109-16, 39(2).

Daniell et al., Milestones in chloroplast genetic engineering: an environmentally friendly era in biotechnology, Trends in Plant Science, 2002, 84-91, 7.

Daniell et al., Multigene engineering, dawn of an exciting new era in biotechnology, Current Opinion in Biotechnology, 2002, 136-141, 13.

Kim et al., Protein Disulfide Isomerase as a Regulator of Chloroplast Translational Activation, Science, 1997, 1954-57, 278.

Muller et al., Functional role of type I and type II interferons in antiviral defense, Science, 1994, 1978-1921, 264.

Svab et al., High frequency plastid transformation in tobacco by selection for a chimeric aadA gene, Proc. Natl. Acad. Sci. USA., 1993, 913-917, 90.

Tompkins et al., Immunomodulation and therapeutic effects of the oral use of interferon-alpha: mechanism of action, Journal of interferon and cytokine research., 1999, 817-828, 19(8).

Sijmons et al., Production of Correctly Processed Human Serum Albumin in Transgenic Plants, Biotechnology,1990, 217-221, 8.

Boston et al., Molecular Chaperones and Protein Folding in Plants, Plant Molecular Biology, 1996, 191-222, 32.

Crickmore et al., Revision of the Nomenclature for the Bacillus thuringiensis Pesticidal Crystal Proteins, Microbiology and Molecular Biology Reviews, 1998, 807-813, 62.

Kota et al., Overexpression of Bacillus thuringiensis (Bt) Cry2Aa2 Protein in Chloroplast Confers Resistance to Plants Against Susceptible and BI-resistant Insects, Proc. Natl. Acad. Sci. USA, 1999, 1840-1845, 96.

Heifetz, Genetic Engineering of the Chloroplast, Biochimie, 2000, 655-666, 82.

Kanno, A Transcription Map of the Chloroplast Genome from Rice (*Oryza sativa*), Curr Genet., 1993, 166-174, 23, 2.

Arlen et al., Effective plague vaccination via oral delivery of plant cells expressing F1-V antigens in chloroplasts, Infect Immun., 2008, 76(8), 3640-50.

Daniell et al., The complete nucleotide sequence of the cassava (*Manihot esculenta*) chloroplast genome and the evolution of atpF in Malpighiales: RNA editing and multiple losses of a group II intron, Theor Appl Genet., 2008, 116(5) 723-37.

Chebolu et al., Stable expression of Gal/GalNAc lectin of Entamoeba histolytica in transgenic chloroplasts and immunogenicity in mice towards vaccine development for amoebiasis, Plant Biotechnol J., 2007, 5(2), 230-9.

Daniell et al., Transgene containment by maternal inheritance: effective or elusive? Proc Natl Acad Sci U S A, 2007, 104(17), 6879-80.

Molina et al., High-yield expression of a viral peptide animal vaccine in transgenic tobacco chloroplasts, Plant Biotechnol J., 2004, 2(2), 141-53.

Ruhlman et al., Expression of cholera toxin B-proinsulin fusion protein in lettuce and tobacco chloroplasts—oral administration protects against development of insulitis in non-obese diabetic mice, Plant Biotechnol J., 2007, 5(4), 495-510.

Verma et al., Chloroplast vector systems for biotechnology applications, Plant Physiol., 2007, 145(4), 1129-43.

Daniell et al., Chloroplast genetic engineering, Biotechnol J., 2006, 1(1), 26-33.

Lee et al., Plastid transformation in the monocotyledonous cereal crop, rice (*Oryza sativa*) and transmission of transgenes to their progeny, Mol Cells., 2006, 21(3), 401-10.

Limaye et al., Receptor-mediated oral delivery of a bioencapsulated green fluorescent protein expressed in transgenic chloroplasts into the mouse circulatory system, FASEB J., 2006, 20(7), 959-61.

Daniell et al., Breakthrough in chloroplast genetic engineering of agronomically important crops, Trends Biotechnol., 2005, 23(5), 238-45.

Koya et al., Plant-based vaccine: mice immunized with chloroplast-derived anthrax protective antigen survive anthrax lethal toxin challenge, Infect Immun., 2005, 73(12), 8266-74.

Quesada-Vargas et al., Characterization of heterologous multigene operons in transgenic chloroplasts: transcription, processing, and translation, Plant Physiol., 2005, 138(3), 1746-62.

Kumar et al., Stable transformation of the cotton plastid genome and maternal inheritance of transgenes, Plant Mol Biol., 2004, 56(2), 203-16.

Kumar et al., Plastid-expressed betaine aldehyde dehydrogenase gene in carrot cultured cells, roots, and leaves confers enhanced salt tolerance, Plant Physiol., 2004, 136(1), 2843-54.

Watson et al., Expression of Bacillus anthracis protective antigen in transgenic chloroplasts of tobacco, a non-food/feed crop, Vaccine, 2004, 22(31-32), 4374-84.

Daniell et al., Multigene engineering: dawn of an exciting new era in biotechnology, Curr Opin Biotechnol., 2002, 13(2), 136-41.

Daniell et al., Milestones in chloroplast genetic engineering: an environmentally friendly era in biotechnology, Trends Plant Sci., 2002, 7(2), 84-91.

* cited by examiner

Western IFN-α

1: IFN-α2 (Intron A)
3-4: IFN-α2 transgenic tobacco plant
6-7: Non-transgenic tobacco plant 1: Molecular weight
2-3: Uninduced HeLa cells
4-5: HeLa cells plus non-transgenic tobacco plant extracts
6-7: HeLa cells plus Intron A
8-9: HeLa cells plus IFN-α2 transgenic tobacco plant extracts

EXPRESSION OF HUMAN INTERFERON IN TRANSGENIC CHLOROPLASTS

This application is a continuation application of U.S. application Ser. No. 10/520,104 filed Jan. 23, 2006 which is a §371 filing of PCT/US03/20869 filed Jul. 2, 2003 which claims benefit of U.S. Provisional Application 60/393,438 filed Jul. 3, 2002. The 10/520,104 application is also a continuation in part application of 09/807,742 filed Apr. 18, 2001, now abandoned, which is §371 of PCT/US01/06288 filed Feb. 28, 2001 which claims benefit of U.S. Provisional applications 60/185,987 filed Mar. 1, 2000 and 60/263,473 and 60/263,668 each filed Jan. 23, 2001. The 10/520,104 application is also a continuation in part of 09/079,640 filed May 15, 1998, now U.S. Pat. No. 7,129,391.

FIELD OF THE INVENTION

This application relates to the field of genetic engineering of plant plastid genomes, particularly chloroplast, vectors for transforming plastids, transformed plants, progeny of transformed plants, and to methods for transforming plastid genomes of plants to generate Human Interferon (IFN).

BACKGROUND

Interferons are in a special class of antiviral proteins secreted in minute amounts from mammalian cells upon induction with viruses, double-stranded RNAs, immunotoxins, mitogenes, etc. There are two main types of interferon: type I represented by the interferons α (lymphocyte interferon) and β (fibroblasts interferon) and type II (or immune interferon) represented by the interferon γ (IFN). The interferon family has been extremely well characterized in the prior art (Haus, L., Archivum Immunologiae et Therapiae Experimentalis, 2000, 48, 95-100.).

The interferon (IFN) system is one of the major mechanisms involved in human immunity. Interferons (IFNs) are a family of related cytokines that mediate a range of diverse functions including antiviral, antiproliferative, antitumor, and immunomodulatory activities. Its disregulation may result in a greater tendency to infectious diseases and to the development of cancer. Genes of interferon system proteins are often located at the sites of breakpoints of the structural chromosome aberrations in cancer.

IFN's are pH stable interferons produced by leukocytes and fibroblasts in response to viral infections. Both alpha and beta IFN belong to class I interferons. The IFNα gene family (about 26 genes, including pseudogenes) and the IFNβ gene are located at band 21 of the chromosome 9 short arms (9p21) the latter more distally than the former29. IFNα and IFNβ are intronless genes originating from a common ancestor gene. (Jaramillo et al., (1995): The interferon system. A review with emphasis on the role of PKR in growth control. Cancer Invest., 13, 327-338; MCK KU@ SICK V. A. (1998): Mendelian inheritance in man. A catalog of human genes genetic disorders. 12th ed. The Johns Hopkins Univ. Press, Baltimore-London.). The human interferon gene family is fully described in this and other references cited throughout the entirety of this application. More specifically, the art has described in detail a number of IFN genes. These genes are well characterized and described in the art. Furthermore, a study of Annu Rev Biochem. 1998; 67:227-64, reveals a number of interferon genes and how cells respond to interferons. These publications are hereby fully incorporated by reference. Furthermore, Henco et al., in J Mol Biol. 1985 Sep. 20; 185(2):227-60, isolated and characterized DNA segments containing IFN-alpha-related sequences from human lambda and cosmid clone banks. They described six linkage groups comprising 18 distinct IFN-alpha-related loci, and report the nucleotide sequences of nine chromosomal IFN-alpha-genes with intact reading frames, as well as of five pseudogenes. Still a further reference which describes a number of the interferon genes is Archivum Immunologiae et Therapiae Experimentalis, 2000, 48, 95-100P L ISSN 0004-069X, The Genes of Interferons and Interferon-Related Factors: Localization and Relationships with Chromosome Aberrations in Cancer. Still, another paper, Biopolymers. 2000; 55(4):254-87, provides a review of the history of the alpha related IFN. The human interferon gene cluster on the short arm of chromosome 9 comprises 26 genes the functional members of which are separated by highly efficient scaffold.

Recombinant IFNα2b is being used for the treatment of Hepatitis B and C for several types of cancer. However, the IFNα2b drugs that are being marketed are produced through an *E. coli* expression system and due to necessary in vitro processing and purification, the average cost of treatment is $26,000 per year. Patients are normally injected with the drugs, Intron®A and PEG-Intron™, resulting in severe side effects which have been linked to route of administration. Because oral delivery of natural human IFNα2b has been shown to elicit a systemic immune response without the negative side effects, it is desirable to create an analogue to natural human IFNα2b that is suitable for oral administration to mammals.

The microbial species used to produce the IFNα2b is marketed under the names PEG-Intron™ and Intron®A is *E. coli*. Prokaryotic expression systems have many advantages as production systems for heterologous proteins. They can be cultured in large quantities inexpensively and in a short time by standard methods of fermentation (Walsh, 1998). In addition, *E. coli* has been well characterized, with over 40 recombinant proteins produced in *E. coli* already approved for general medical use (Walsh, 2000).

However, many eukaryotic proteins cannot be expressed in prokaryotic hosts because their mRNAs contain introns that need to be removed in order for correct translation and *E. coli* is unable to process these transcripts (Glick and Pasternak, 1998). The IFNαs are unusual for eukaryotic proteins in that they contain no introns, and so processing is not necessary. Although numerous IFN α subtypes have been expressed in *E. coli*, special techniques that add to the cost of the drug have to be employed to produce the mature, biologically active interferon. Prokaryotic systems cannot form disulfide bonds when IFNα is produced intracellularly and consequently it cannot fold properly (Thatcher and Panayotatos, 1986). As a result, the IFNαs, such as IFNα2b, aggregate to form inclusions bodies that need to be solubilized (Swaminathan and Khanna, 1999). Additional downstream processing steps include purification and formation of proper disulfide bonds (Walsh, 1998). Besides *E. coli*, low levels of IFNα2 have been expressed in silkworm using a baculovirus vector (Maeda et al., 1985) and into a phage vector (Slocombe et al., 1982).

For several viruses and cancers, the only treatment approved by the FDA is injections of IFNα2b. However, the treatment has many side effects and only 20% of patients who need treatment can actually afford to buy the drug (Harris-Stuart and Penny, 1997). Consequently, alternative means of producing IFNα2 have been explored.

Although bacterial and fungal systems are the most predominant systems for commercial production of recombinant proteins, they have several important drawbacks when producing proteins from eukaryotes. Proteins that require disulfide bonds or glycosylation are not well suited for expression in microorganisms (Glick and Pasternak, 1998). A recombinant protein can be toxic to the microorganism, form inclusion bodies, or be degraded by proteases (Kusnadi et al., 1997). Transgenic plants are potentially one of the most economical systems for large-scale production of recombinant proteins for industrial and pharmaceutical uses (Walmsley and Arntzen, 2000).

Unique to plants is the ability to regenerate whole plants from cells or tissues. This totipotency has many practical benefits: for example, plants propagated by seed can be cultured in vitro to yield thousands of identical plants (Bhojwani, 1990). In particular, tobacco is the easiest plant to genetically engineer and is widely used to test suitability of plant-based systems for bioproduction of recombinant proteins. Tobacco is an excellent biomass producer (in excess of 40 tons leaf fresh weight/acre based on multiple mowings per season) and a prolific seed producer (up to one million seeds produced per plant), thus hastening the time in which a product can be scaled up and brought to market (Cramer et al., 1998). In general, plant systems are more economical than industrial facilities using fermentation or bioreactor systems and the technology is already available for harvesting and processing plants and plant products on a large scale (Daniell et al., 2001a). Plant-derived products are less likely to be contaminated with human pathogenic microorganisms than those derived from animal cells because plants don't act as hosts for human infectious agents (Giddings et al., 2000).

Recombinant proteins expressed in plant cells are naturally protected from degradation when taken orally (Kong et al., 2001). Oral delivery is highly desirable for drug treatment (Gomez-Orellan and Paton, 1998). Oral administration of natural human IFNα has proven to be therapeutically useful in the treatment of various infectious diseases and low doses of recombinant IFNαs were shown to be effective as well (Tompkins, 1999).

The genetic information of plants is distributed among three cellular compartments: the nucleus, the mitochondria, and the plastids and each of these carries its own genome and expresses heritable traits (Bogorad, 2000). Transformation of the plant nucleus is routine in many species and there are a variety of techniques for delivering foreign. DNA to the plant nuclear genome (Hager and Bock, 2000). However, recombinant protein expression in plants by nuclear transformation have been low, with most levels much less than the 1% of total soluble protein that is needed for commercial feasibility if the protein must be purified (Daniell et al., 2002). For example, only 0.000017% of transgenic tobacco leaves was IFN (Elderbaum et al., 1992). Also, negligible amounts of IFNα was produced in nuclear transformation of rice (Zhu et al., 1994). In addition, with nuclear expression, the foreign protein levels vary in transgenic lines because the foreign gene is inserted randomly into different locations (Bogorad, 2000). Other factors that lower expression levels are the gene silencing and position effects so often observed in nuclear transgenic plants (Daniell and Dhingra, 2002).

The plastids of plants are an attractive target for genetic engineering. Plant plastids (chloroplasts, amyloplasts, elaioplasts, etioplasts, chromoplasts, etc.) are the major biosynthetic centers that, in addition to photosynthesis, are responsible for production of industrially important compounds such as amino acids, complex carbohydrates, fatty acids, and pigments. Plastids are derived from a common precursor known as a proplastid and thus the plastids present in a given plant species all have the same genetic content. In general, plant cells contain 500-10,000 copies of a small 120-160 kilobase circular plastid genome, each molecule of which has a large (approximately 25 kb) inverted repeat. Thus, it is possible to engineer plant cells to contain up to 20,000 copies of a particular gene of interest which can result in very high levels of foreign gene expression.

The modern chloroplast of plants has retained a largely prokaryotic system of gene organization and expression, with the eukaryotic nuclear genome exerting significant regulatory control (Hager and Bock, 2000). Signaling pathways have evolved to coordinate gene expression between the chloroplast and the nuclear-cytosolic compartments during chloroplast development and in response to environmental factors such as light (Zerges, 2000). Illuminated chloroplasts possess extraordinarily high rates of transcription and translation that is tissue-specific due to regulation via untranslated regions of chloroplast-encoded mRNAs. Although communication between the chloroplast and the nucleus exist, these membrane-separated genetic systems have their own distinct environmental milieu containing different proteins, proteases and mechanisms of action. Unique features of the photosynthetic plastid enable genetic engineering of the chloroplast to overcome major limitations of plant nuclear transformation technology.

One major concern with the genetic modification (GM) of plants is the possibility of the escape of foreign genes through pollen dispersal from transgenic plants to sexually compatible weedy relatives or to pathogenic microbes in the soil (Daniell, 2002). Such gene transfers could potentially result in the emergence of "superweeds" able to resist certain herbicides thereby undermining the benefits of GM crops (Daniell, 2002). However, genes in the chloroplasts of higher plants are generally transmitted only by the maternal parent, which means that chloroplast genes are not present in the pollen (Bogorad, 2000). Therefore, a foreign gene introduced by genetic engineering of the chloroplast genome could not transfer to genetically compatible weeds. This uniparental or maternal inheritance provides the gene containment necessary for keeping foreign genes sequestered in target plants and preventing gene flow among crops and weeds (Daniell, 2002).

Another remarkable feature of the plastid genome is its high ploidy level: a single tobacco leaf cell may contain as many as 100 chloroplasts, each harboring approximately 100 identical copies of the plastid genome, resulting in an extraordinarily high ploidy degree of up to 10,000 plastid genomes per cell (Bogorad, 2000). Because of the very high ploidy level of the plastid genome, very high expression levels can be achieved. For example, the *Bacillus thuringiensis* (Bt) Cry2Aa2 protein accumulated as cuboidal crystals in transgenic chloroplasts and reached a level of 45.3% of the tsp in mature leaves (De Cosa et al., 2001).

For transformation of chloroplasts in plants, particle bombardment is used to introduce transgenes into leaf chloroplasts and stable transformation requires that 10,000 chloroplast copies be uniformly converted (Bock and Hagemann, 2000). Securing genetically stable lines of plants with transgenic chloroplast requires every chloroplast to carry the inserted gene (Bogorad, 2000). This homoplasmic state is achieved through amplification and sorting of transgenic chloroplasts with the elimination of the wild-type copies on selective medium (Maliga, 1993). The integration of cloned plastid DNA into the plastid genome occurs through site-specific homologous recombination in plants such as in tobacco *N. tabacum* and excludes the foreign vector DNA (Kavanagh et al., 1999). In contrast, nuclear transformation experiments in higher plants frequently suffer from epigenetic gene-silencing mechanisms resulting in inconsistent and unstable gene expression or complete loss of transgenic activity (Hager and Bock, 2000). The nuclear genome has mechanisms to effectively inactivate genes when regulatory sequences are inserted in a repetitive pattern and this occurs because integration of transgenes into the nuclear genome is random and through non-homologous recombination (Daniell and Dhingra, 2002). Random integrations of transgenes also means that the final location of the inserted gene may be in a region of the nuclear genome that is not highly transcribed. As a consequence, nuclear expression levels vary in different transgenic lines and these differences are due to the inserted gene's random position in the nuclear genome. Neither gene silencing nor position effects have been observed in genetically engineered chloroplasts may be in region of the nuclear genome that is not highly transcribed. As a consequence, nuclear expression levels vary in different transgenic lines and these differences are due to the inserted gene's random position in the nuclear genome. Neither gene silencing nor position effects have been observed in genetically engineered chloroplasts (Daniell and Dhingra, 2002). Another major advantage of chloroplast engineering is the expression of multiple transgenes as operons due to efficient translation of polycistronic messenger RNAs (De Cosa et al., 2001). Genetic engineering has now moved from introducing single gene traits to coding for complete metabolic pathways, bacterial operons, and biopharmaceuticals that require assembly of complex multisubunit proteins (Daniell, 2002).

Disulfide bonds are common to many extracellular proteins because they stabilize the native conformation by lowering the entropy of the unfolded form (Abkevich and Shakhnovich, 2000). Most proteins need to be folded correctly for the protein to function properly and remain in solution. Eukaryotic secretory proteins are normally routed through the endoplasmic reticulum where disulfide bond formation occurs. Experiments show that chloroplasts have the machinery needed to fold complex eukaryotic secretory proteins in the soluble chloroplast stroma compartment. The activities of several chloroplast enzymes involved in the anabolic processes of carbon assimilation are enhanced or triggered by light through a signaling system called the ferredoxin-thioredoxin system (Ruelland and Miginiac, Maslow, 1999). Two correct disulfide bonds were formed in the tobacco chloroplast expression of human somatotropin. In another study, binding assays confirmed that chloroplast-synthesized cholera toxin of *Vibrio cholera* (CTB) bound intestinal receptors indicating that correct folding and disulfide bond formation had occurred (Daniell et al., 2001). The light signal sensed by chlorophyll is transferred via the photosynthetic electron flow to proteins called thioredoxins, which are very efficient in thio-disulfide interchanges with various protein disulfides (Ruelland and Miginiac-Maslow, 1999). Another mechanism for the simple, reversible activation of genes that regulate expression in the chloroplast is the Protein Disulfide Isomerase (PDI) system composed of chloroplast polyadenylate-binding proteins that specifically bind to the 5'UTR of the psbA mRNA and are modulated by redox status through PDI (Kim and Mayfield, 1997). The ability of chloroplasts to form disulfide bonds and properly fold foreign proteins eliminates a major part of the costly downstream processing.

Expression of functional human somatotropin in transgenic tobacco chloroplasts established that chloroplasts are capable of proper folding of human proteins with disulphide bonds. The ability to express multiple genes in a single transformation event (Daniell and Dhingra, 2002; De Casa et al., 2001), accumulation of exceptionally large quantities of foreign proteins (De Casa et al., 2001), successful engineering of tomato chromoplasts for high level transgene expression in fruits (Ruf et al., 2001, or carrots (Kumar et al., 2003), coupled to hyper-expression of vaccine antigens (Daniell et al., 2001b), and the use of plant derived antibiotic free selectable markers (Daniell et al., 2001c), augur well for oral delivery of edible vaccines and biopharmaceuticals that are currently beyond the reach of those who need them most. The term "edible vaccine" or "oral delivery" as used herein refers to a substance which may be given orally which will elicit a protective immunogenic response in a mammal.

Good recombinant systems are still not available for many human proteins that are expensive to purify or highly susceptible to proteolytic degradation. It is known that traditional purification of biopharmaceuticals proteins using columns accounts for 30% of the production cost and 70% of the set up cost (Petrides et al., 1995). Proteolytic degradation is another serious concern for industrial bioprocessing. The increasing production of proteins in heterologous hosts through the use of recombinant DNA technology has brought this problem into focus; heterologous proteins appear to be more prone to proteolysis (Enfors, 1992). Recombinant proteins are often regarded by a cell as foreign and therefore degraded much faster than most endogenous proteins (Rozkov et al., 2000). Proteolytic stability of recombinant proteins is a significant factor influencing the final yield. In view of these limitations, the Applicant has developed a more efficient method for producing a recombinant biopharmaceutical protein, such as IFNα2b production, which may be used as a model system to enrich or purify biopharmaceutical proteins from transgenic plants, which are highly susceptible to proteolytic degradation.

To date no one has successfully transformed the plastid genome with IFN to create a delivery system that is easily administered and that stimulates both arms of the immune system without the severe side effects experienced by patients in current IFNα2b treatments. In addition, until the Applicant's discovery, production vehicles (*E. coli*, nuclear plant genomes, etc. . . . ) have failed to provide a cost effective and functional IFN, which can be orally administered without the side effects, i.e., human pathogens that are associated with the current production vehicles. In view of these limitations the Applicant developed a system for the expression of interferon, such as IFNα2b, via the chloroplast genome in order to provide a feasible means of overproducing this increasingly useful therapeutic drug as well as addressing current concerns with the present methods of delivery and production. Also incorporated by reference into this application is the utility application, based off of U.S. Provisional Application No. 60/393,651, and filed simultaneously with this application. Still another application, PCT/US02/41503, filed on Dec. 26, 2002, is also incorporated by reference into this application. These applications describe in detail, somatic embryogenosis for the construction of edible vaccines.

SUMMARY OF THE INVENTION

One aspect of the invention is the creation of a plastid transformation vector for a stably transforming a plastid. The vector comprises, as operably-linked components, a first flanking sequence, a DNA sequence coding for a human therapeutic interferon (IFN) or a substantially homologous DNA sequence of IFN, which is capable of expression in said plastid genome, and a second flanking sequence. A second aspect provides a method for producing IFN. The method includes the steps of integrating the plastid transformation vector described above into the plastid genome of a plant cell, and then growing the plant cells to express IFN, and testing their functionality.

Still another aspect of the invention is an isolated and purified IFN derived from a chloroplast which has been transformed with the vector described above. Another aspect provides for an orally administrable therapeutic human interferon recombinant IFN, which is suitable for oral administration to a mammal. Yet another aspect of the invention provides for transformed plants, plant parts, plant cells and the progeny thereof, which are capable of expressing IFN. Still another aspect of this invention relates to the vector above described aspects, wherein IFNα2b, is utilized.

BRIEF DESCRIPTION OF THE FIGURES

FIG. 1(A) shows a schematic of the pLD-RF-IFNα2b vector designed for chloroplast transformation. Each of the two primer sets illustrated to indicate the location and size of the resulting PCR product. The trnl and trnA genes were used as flanking sequences for homologous recombination. The constitutive 16s rRNA promoter was used to regulate transcription. The aadA gene conferring spectinomycin resistance was used for selection of transgenic shoots. The IFNα2b gene was regulated by the psbA promoter and 5' (5UTR) and 3' UTR (T) elements.

FIG. 1(B) shows an 0.8% agarose gel illustrating the 1.65 kb PCR product utilizing 3P/3M primers. Lane 1: Ladder; Lane 2: Negative control wild type tobacco plant DNA; Lane 3: Mutant; Lane 4-8: 5 different transgenic lines tested; Lane 9: Positive transgenic plant DNA.

FIG. 1(C) shows an 0.8% agarose gel illustrating 2.3 kb PCR product utilizing 5P/2M primers. Lane 1: Ladder; Lane 2: Negative control wild type tobacco plant DNA; Lane 3: Positive control (2 ug of pLD-RF-IFNα2b); Lane 4-10: Different transgenic lines tested; Lane 9-10: Questionable transgenic plants with no PCR product; Lane 11: Ladder.

FIG. 2(A) shows a schematic of the pLD-RF-IFNα2b vector designed for chloroplast transformation, with each of the two primer sets illustrated to indicate the location and size of the resulting PCR product.

FIG. 2(B) shows an 0.8% agarose gel illustrating 1.65 kb PCR product utilizing 4P/4M primers. Lane 1: Positive control; Lane 2: Negative control, untransformed LAMD-609; Lane 3; Ladder; Lane 4-11: Different transgenic lines tested.

FIG. 2(C) shows an 0.8% agarose gel illustrating 2.3 kb PCR product utilizing 5P/2M primers. Lane 1: Positive control; Lane 2: Negative control, untransformed LAMD-609; Lane 5, 8, 9, and 11: Different transgenic lines tested.

FIG. 3(A) 810 bp probe containing chloroplast flanking sequences. FIG. 3(B) DNA fragments of 7.9 kbp indicate no transformed chloroplast and DNA fragments of 9.9 kbp are observed when the chloroplast genome has the transgenes integrated.

FIG. 4(A) shows a low-nicotine tissue extracts separated on 15% SDS-PAGE with IFNα2b detected by mouse monoclonal antibody against human IFNα. Lane 1: 80 ng of PEG-Intron standard; Lane 2: Protein marker; Lane 3: Untransformed LAMD-609; Lanes 4-7: Transgenic LAMD-609 lines expressing monomers and multimers of IFNα2b.

FIG. 4(B) shows a Western blot of Petit Havana transgenic chloroplasts expressing IFNα2b. Petit Havana leaf extracts separated on 15% SDS-PAGE with IFNα2b detected by mouse monoclonal antibody against human IFNα. Lane 1: 38 ng Intron®A standard; Lane M: Protein marker; Lane 2: 190 ng Intron®A standard; Lane 3: Untransformed Petit Havana; Lanes 4-6: Transgenic Petit Havana lines expressing monomers and multimers of IFNα2b; Lanes 7-8: *E. coli* transformed with IFNα2b.

FIG. 5 (A) shows protein quantification by ELISA in young, mature and old transgenic leaves of Petit Havana (2C, 3C, and 5 are independent transgenic lines). FIG. 5(B) Protein quantification by ELISA in young LAMD-609 (2, 5, 9 and 10 are independent transgenic lines).

FIG. 10A shows the Northern blot with transgenic lines expressing high levels of IFN in black and low levels in red. Probe: IFN. Ethidium bromide stained 25S RNA was used to assess loading.

FIG. 10B shows the Cooomassie stained SDS-PAGE. Transgenic lines expressing high levels of IFN in black and low levels in red. TSP: total soluble protein and TP: total protein.

DETAILED DESCRIPTION

Figure 1A:
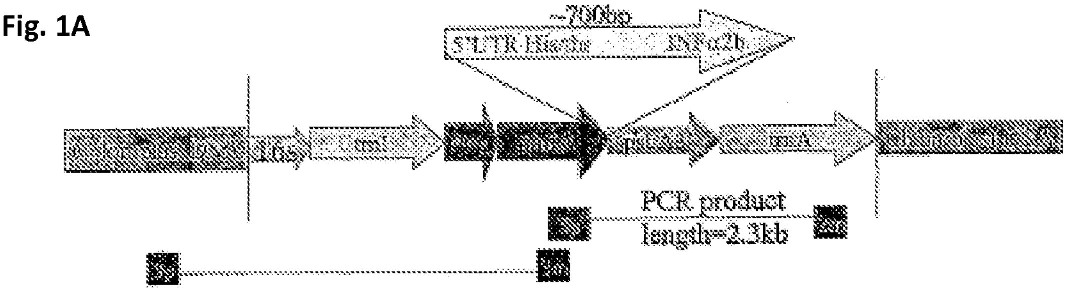
FIG. 1(A)-FIG. 1(C) show the pLD-RF-IFNα2b vector, and PCR analysis of putative petit havana transgenic lines.

In one aspect, vectors are provided, which can be stably integrated into the plastid genome of plants for the expression of IFN. In another aspect, methods of transforming plastid genomes to express IFN, transformed plants and progeny thereof, which variable-express IFN are provided. Still another aspect provides for methods of expressing biopharmaceutical proteins using selected regulatory elements. Another aspect provides for methods and constructs which protect biopharmaceutical proteins from proteolytic degradation. Still another aspect of this invention provides for the creation of orally administrable IFN.

Preferred embodiments of this invention are applicable to all plastids of plants. These plastids include the chromoplasts, which are present in the fruits, vegetables, and flowers; amyloplasts which are present in tubers such as potato; proplastids in the roots of higher plants; leucoplasts and etioplasts, both of which are present in the non-green parts of plants, and the plastids of such organisms as algae, which contain plastids.

Definitions

To better understand the current disclosure, the following definitions, which are provided for background purposes and in no way are to be construed as a limitation, are provided to put the application in proper context.

"Variable-expression" should be understood to mean the expression of IFN, which yields a broad range of soluble proteins of IFN from a stably transformed plant.

"Properly folded" should be understood to mean a protein that is folded into its normal conformational configuration, which is consistent with how the protein folds as a naturally occurring protein expressed in its native host cell.

"Regulatory sequence" should be understood to be a DNA base sequence that aids in the control of gene expression. A regulatory sequence may aid in such things as promoting, enhancing, terminating, stabilizing, modifying, or variable-expressing gene expression in a plant plastid, and or plant cell. A regulatory sequence may also play a role in folding a gene product (e.g. a protein or enzyme, or may play a role in placing the gene product within an inclusion body, or any of a number of roles, which will provide transcript stability. As a non limiting example of regulatory sequences, there is psbA region, cry2Aa2 untranslated region (UTR), UTR's, both 5' and 3' functional within plant plastids, the Shine Delgano sequence (SD), 16srRNA, and plastid specific promoters (which are well characterized and described in the art).

"Stably integrated DNA sequences (or genes)" are those DNA sequences which are inherited through genome replication by daughter cells or organisms. This stability is exhibited by the ability to establish permanent cell lines, clones, or transgenic plants comprised of a population containing the exogenous DNA sequence(s). U.S. Pat. No. 5,693,507 to Daniell and Mcfadden discloses such stable integration, which is fully incorporated by reference.

An "edible plant" is any plant which is suitable for mammal consumption.

The term "edible" as used herein when referring to biopharmaceutical proteins, or IFN, refers to a substance which may be given orally and which will elicit an immunogenic response in a mammal.

"Substantially homologous" as used throughout the ensuing specification and claims, is meant a degree of homology to the native IFN sequence in excess of 70%, most preferably in excess of 50%, and even more preferably in excess of 90%, 95% or 99%. Substantial sequence identity or substantial homology as used herein, is used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include, for example, ability to maintain expression and properly fold into the proteins conformational native state, hybridize under defined conditions, or demonstrate a well defined immunological cross-reactivity, similar biopharmaceutical activity, etc. Each of these characteristics can readily be determined by the skilled practitioner in the art using known methods. Locating the parts of these sequences that are not critical may be time consuming, but is routine and well within the skill in the art.

"Spacer region" is understood in the art to be the region between two genes. The chloroplast genome of plants contains spacer regions which highly conserved nuclear tide sequences. The highly conserved nature of the nucleotide sequences of these spacer regions chloroplast genome makes the spacer region ideal for construction of vectors to transform chloroplasts of a wide variety of plant species, without the necessity of constructing individual vectors for different plants or individual crop species. It is well understood in the art that the sequences flanking functional genes are well-known to be called "spacer regions". The special features of the spacer region are clearly described in the Applicant's application Ser. No. 09/079,640 filed May 15, 1998 and entitled UNIVERSAL CHLOROPLAST INTEGRATION OF EXPRESSION VECTORS, TRANSFORMED PLANTS AND PRODUCTS THEREOF. The aforementioned application Ser. No. 09/079,640 is hereby incorporated by reference. It was well-known that there are at least sixty transcriptionally-active spacer regions within the higher plant chloroplast genomes (Sugita, M., Sugiura. M., Regulation of Gene Expression in Chloroplasts of Higher Plants, Plant Mol. Biol., 32: 315-326, 1996). Specifically, Sugita et al. reported sixty transcriptionally-active spacer regions referred to as transcription units, as can be seen in Table II of the article.

Because the transcriptionally active spacer regions are known, a universal vector, as described in the Applicant's U.S. patent application Ser. No. 09/079,640, can be used in the identified spacer regions contained within a variety of the plant chloroplast genomes. By utilizing the teachings in Sugita et al., intergenic spacer regions are easily located in the plastid genome. Consequently, this allows one skilled in the art to use the methods taught in the Applicant's U.S. patent application Ser. No. 09/079,640 to insert a universal vector containing the psbA, the 5' untranslated region (UTR) of psbA and the gene coding for HSA into the spacer regions identified by Sugita et al., and found across plants. The aforementioned applications and articles are incorporated by reference.

"Selectable marker" provides a means of selecting the desired plant cells, vectors for plastid transformation typically contain a construct which provides for expression of a selectable marker gene. "Marker genes" are plant-expressible DNA sequences which express a polypeptide which resists a natural inhibition by, attenuates, or inactivates a selective substance, i.e., antibiotic, herbicide, or an aldehyde dehydrogenase such as Betaine aldehyde dehydrogenase (described in the Applicant's application Ser. No. 09/807,722 filed Apr. 18, 2001, and fully incorporated herein by reference). The use of an antibiotic free selectable marker has allowed for the possibility of oral delivery of biopharmaceutical proteins. Oral delivery through a transformed edible plant has been demonstrated in Applicant's International Application No. PCT/US02/41503, which is fully incorporated herein by reference.

Alternatively, a selectable marker gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts or whole plants containing the construct. Detection of the marker phenotype makes possible the selection of cells having a second gene to which the marker gene has been linked.

The use of such a marker for identification of plant cells containing a plastid construct has been described in the literature. In the examples provided below, a bacterial aadA gene is expressed as the marker. Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Numerous additional promoter regions may also be used to drive expression of the selectable marker gene, including various plastid promoters and bacterial promoters which have been shown to function in plant plastids.

"Inverted Repeat Regions" are regions of homology, which are present in the inverted repeat regions of the plastid genome (known as IRA and IRB), two copies of the trans gene are expected per transformed plastid. Where the regions of homology are present outside the inverted repeat regions of the plastid genome, one copy of the transgene is expected per transformed plastid.

"Structural(ly) equivalent" should be understood to mean a protein maintaining the conformational structure as the native protein expressed in its natural cell.

"Native conformation" is the conformation in which a molecule is biologically active.

When referring to the relative age of the plants, plant parts and leaves, well followed principles in the art should be applied. Young, mature and old plants are considered in the cycle of plant life. Young reproductive plants exhibit more new growth than death of old parts. Mature plants exhibit a balance between growth and death of parts. These plants usually have the greatest yearly seed production and biomass increase (increase in weight). In other words, they are at their peak. In old plants, the death of parts prevails over the production of new parts. Reproductive activity is diminished. Proteolytic activity in each of these stages must be considered when transforming the plastid genome to express an exogenous non-native gene in plant plastids.

Exemplary Vectors Suitable for use

This invention contemplates the use of vectors capable of plastid transformation, particularly of chloroplast transformation. Such vectors include chloroplast expression vectors such as pU, pBR322, pBLUESCRIPT, pGEM, and all others identified by Daniell in U.S. Pat. Nos. 5,693,507 and 5,932,479. Included are also vectors whose flanking sequences are located outside of the inverted repeat of the chloroplast genome. These publications and patents are hereby incorporated by reference to the same extent as if each individual publication or patent was specifically an individually indicated to be incorporated by reference.

The universal vector is described in WO 99/10513 which was published on Mar. 4, 1999, and application Ser. No. 09/079,640 which was filed on May 15, 1998, wherein both of said references are incorporated in their entirety.

As an illustrative embodiment for the vectors, the Applicants created one vector to transform *Nicotiana tabacum* cv. Petit Havana, and LAMD-609 (low nicotine tabacco variety). The exemplary vector was created with the 700 bp IFNα2b gene cassette to contain both the thrombin cleavage site and a polyhistidine tag.

This also includes carrot plastid transformation (PCT Application No. PCT/US/02/41503, filed Dec. 26, 2002) for high level transgene expression in chromoplasts. The exemplary vector was created with the 700 bp IFNα2b gene cassette to contain both the thrombin cleavage site and a polyhistidine tag.

General Methodology for Transforming the Plastid Genome

This illustrative example shows generally all of the necessary steps to practice this invention. Of course other suitable methods, which are known in the art may be substituted or used to supplement the example methodology described herein.

Isolation of Genomic DNA from Plants.

Mortar and pestle, liquid nitrogen, fresh dark green leaves.

DNeasy Plant Mini Kit (QIAGEN Inc.)

PCR Amplification of Chloroplast Flanking Sequence.

Materials for PCR reaction: Genomic DNA (50-100 ng/μL), dNTPs, 10×pfu buffer, Forward primer, Reverse primer, autoclaved distilled $H_2O$ and Turbo pfu DNA Polymerase.

Vector Construction.

1. Plasmid pUC19 or pBlueScript SK (+/−).
2. Species specific PCR amplified chloroplast DNA flanking sequences.
3. A promoter functional in plastids, 5'UTR of chloroplast gene, selectable marker gene, gene of interest and chloroplast 3'UTR.
4. Restriction enzymes and buffers.
5. T4 DNA polymerase to remove 3' overhangs to form blunt ends and fill-in of 5' overhangs to form blunt ends or Kienow large fragment (fill-in of 5' overhangs to form blunt ends), alkaline phoshatase for dephoshorylation of cohesive ends, DNA ligase to form phosphodiester bonds and appropriate buffers.
6. Water baths or incubators set at different temperatures.

Preparation for Biolistics.

1. Autoclaved Whatman filter paper #1 (55 mm in diameter) dried in oven.
2. 100% ethanol.
3. Autoclaved tips in box, autoclaved kimwipes tissues wrapped in aluminum foil.
4. Sterile gold particles stored at −20° C. in 50% glycerol (see Notes 1 and 2).
5. Sterile rupture discs (1100 psi) and macrocarriers sterilized by dipping in 100% ethanol.
6. Autoclaved steel macrocarrier holders and stopping screens.
7. Freshly prepared 2.5 mM $CaCl_2$: weigh 1.84 g and dissolve in 5 mL $H_2O$ and filter sterilized with 0.2 μm filter.
8. 0.1 M spermidine (highly hygroscopic): dilute IM spermidine stock to 10× and aliquot 100 μL in 1.5 mL Eppendrop tubes to store at −20° C. Discard each tube after single use.

Medium Preparation for Plant Tissue Culture.

2.5.1. Tobacco

Medium for 1000 mL: 4.3 g MS salts (INVITROGEN Inc.), $H_2O$ (molecular biology grade), 100 mg/L myo-inositol, 1 mg/L thiamine-HCl, 3% sucrose for shoot induction and 2% sucrose for root induction, 1 mg/L 6-benzyl aminopurine (BAP; use 1 mL from 1 mg/mL stock), 0.1 mg/L indole-3-acetic acid (use 0.1 mL from 1 mg/mL IAA stock), 1 mg/L indole-3-butyric acid for root induction (use 1 mL from 1 mg/mL IBA stock). Add 500 mg/L spectinomycin in autoclaved medium when it cools to 45° C.-50° C. (use 5 mL filter sterilized spectinomycin from 100 mg/mL stock).

Edible Crops

Potato

Medium for 1000 mL: 4.3 g MS salts, BS vitamins (make 100× solution in 100 mL $H_2O$ by dissolving: 1 g myo-inositol, 10 mg nictonic acid, 10 mg pyridoxine-HCl, 100 mg thiamine-HCl; use 10 mL, store remaining solution at 4° C.), 5 mg/l zeatin riboside (use 0.5 mL from 1 mg/mL ZR stock), 0.1 mg/l a-napthaleneacetic acid (use 0.1 mL from 1 mg/mL NAA stock), 40 to 500 mg/L spectinomycin.

Tomato

Medium for 1000 mL: 4.3 g MS salts, BS vitamins (10 mL from 10× stock), 0.2 mg/l indole-3-acetic acid (use 0.2 mL from 1 mg/mL IAA stock), 3 mg/l of 6-benzylaminopurine (use 3 mL from 1 mg/mL BAP stock). 300 or 500 mg/L spectinomycin.

For all plant growth media adjust to pH 5.8 with 1N KOH or 1N NaOH and add 6 g/L phytagel (Sigma) before autoclaving at 121° C. for 20 min. For preparation of 1 mg/mL stock of BAP, IAA, IBA, NAA, ZR respectively: weigh 10 mg powder and dissolve first in 1 or 2 drops of 1N NaOH and make up the final volume to 10 mL; store all plant growth regulators at 4° C. for 1-2 months).

Molecular Analysis of Transgenic Plants.

PCR Analysis for Gene Integration into Tobacco Chloroplasts

PCR reaction for 50 µL: 1.0 µl genomic DNA (50-100 ng/µl), 1.5 µl dNTPs (stock 10 mM), 5.0 µl (10×PCR buffer), 1.5 µl Forward primer (to land on the native chloroplast genome; stock 10 µM), 1.5 µl Reverse primer (to land on the transgene; stock 10 µM), 39.0 µl autoclaved distilled $H_2O$ and 0.5 µl Taq DNA polymerase.

Analysis of Homoplasmy by Southern Blots.

1. Depurination solution: 0.25 N HCl (use 0.4 mL HCl from 12.1 N HCl; Fisher Scientific USA, to make up final volume 500 mL with distilled $H_2O$).
2. Transfer buffer: 0.4 N NaOH, 1 M NaCl (weigh 16 g NaOH and 58.4 g NaCl and dissolve in distilled $H_2O$ to make up the final volume to 1000 mL).
3. 20×SSC: 3M NaCl, 0.3 M. sodium citrate trisodium salt (weigh 175.3 g NaCl, 88.2 g $Na_3C6H_5O_7.2H_2O$ 900 mL $H_2O$ and adjust pH 7.0 using 1 N HCl and make up the final volume to 1000 mL with distilled $H_2O$ and autoclave).
4. 2×SSC: Add 20 mL of 20×SSC in 180 mL of distilled $H_2O$.

Protein Analysis by Western Blots.

1. Acrylamide/Bis: ready made from Fischer (USA), stored at 4° C.
2. 10% SDS: dissolve 10 g SDS in 90 mL deionized water, make up the volume to 100 mL, store at room temperature.
3. Resolving gel buffer: 1.5 M Tris-HCl (add 27.23 g Tris base in 80 mL water, adjust to pH 8.8 with 6 N HCl and make up the final volume to 150 mL. Store at 4° C. after autoclaving).
4. Stacking gel buffer: 0.5 M Tris-HCl (add 6.0 g Tris base in 60 mL water. Adjust to pH 6.8 with 6 N HCL Make up the volume to 100 mL. Store at 4° C. after autoclaving).
5. Sample Buffer (SDS Reducing Buffer): In 3.55 mL water add 1.25 mL 0.5 M Tris-HCl (pH 6.8), 2.5 mL glycerol, 2.0 mL (10% SDS), 0.2 mL (0.5% Bromophenol blue). Store at room temperature. Add 50 µL β-Mercaptoethanol (βME) to 950 µL sample buffer prior to its use.
6. 10× running buffer (pH 8.3): Dissolve 30.3 g Tris Base, 144.0 g Glycine and 10.0 g SDS in 700 mL water (add more water if not dissolving). Bring up the volume to 1 L and store at 4° C.
7. 10×PBS: Weigh 80 g NaCl, 2 g KCl, 26.8 g $Na_2HPO_47H_2O$ (or 14.4 g $Na_2HPO_4$), 2.4 g $KH_2PO_4$ in 800 mL water. Adjust pH to 7.4 with HCl and make up the volume to 1 L. Store at room temperature after autoclaving.
8. 20% APS: Dissolve 200 mg ammonium persulfate in 1 mL water (make fresh every two weeks).
9. Transfer buffer for 1500 mL: Add 300 mL 10× running buffer, 300 mL methanol, 0.15 g SDS in 900 mL water and make volume to 1 L.

Plant Extraction Buffer:

| | Used Concentration | Final Concentration |
|---|---|---|
| 60 µl | 5M NaCl | 10 mM |
| 60 µl | 0.5M EDTA | 10 mM |
| 600 µl | 1M Tris-HCl | 200 mM |
| 2 µl | Tween-20 | .05% |
| 30 µL | 10% SDS | 0.1% |
| 3 µL | BME | 14 mM |
| 1.2 mL | 1M Sucrose | 400 mM |
| 1 mL | Water | |
| 60 µL | 100 mM PMSF | 2 mM |

Add PMSF just before use (vortex to dissolve PMSF crystals).

PMSF (Phenylmethyl sulfonyl fluoride): Dissolve 17.4 mg of powdered PMSF in 1 mL of methanol by vortexing and store at −20° C. for up to a month.

Methods

Isolation of Genomic DNA from Plants.

Extract the genomic DNA from fresh green leaves using DNeasy Plant kit (QIAGEN Inc.) following vender's instructions.

Amplification of Chloroplast Flanking Sequence.

Species-specific flanking sequences from the chloroplast DNA or genomic DNA of a particular plant species is amplified with the help of PCR using a set of primers that are designed using known and highly conserved sequence of the tobacco chloroplast genome.

Conditions for running PCR reaction: There are three major steps in a PCR, which are repeated for 30 to 40 cycles. (1) Denaturation at 94° C.: to separate double stranded chloroplast DNA. (2) Annealing at 54 to 64° C.: primers bind to single stranded DNA with formation of hydrogen bonds and the DNA polymerase starts copying the template. (3) Extension at 72° C.: DNA Polymerase at 72° C. extends to the template that strongly forms hydrogen bond with primers. Mismatched primers will not form strong hydrogen bonds and therefore, all these temperatures may vary based on DNA sequence homology. The bases complementary to the template are coupled to the primer on the 3' side. The polymerase adds dNTPs from 5' to 3', reading the template in 3' to 5' direction and bases are added complementary to the template.

Chloroplast Transformation Vector.

Figure 10A:
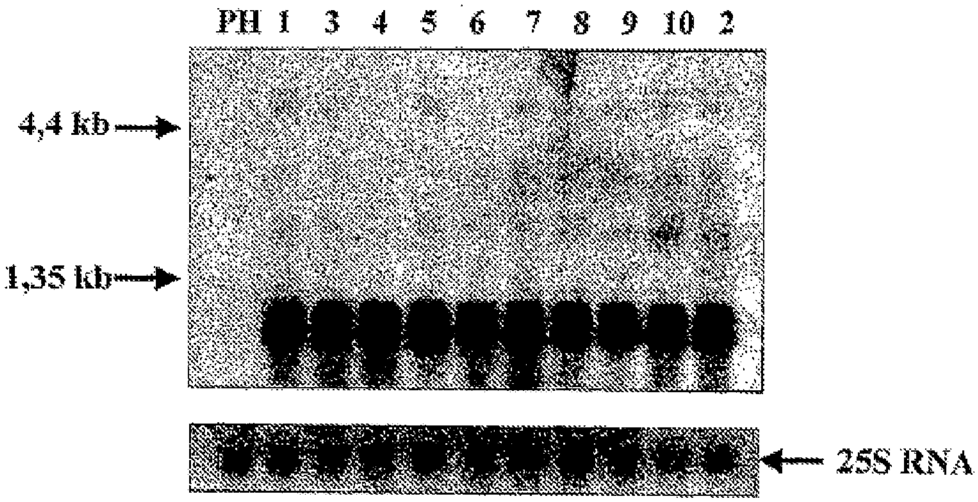
FIG. 10(A)-FIG. 10(B) shows respectively a northern blot and Cooomassie stained SDS-PAGE. More specifically this figure shows that in high expressing transgenic lines up to 27% of IFNα2b was observed and could be seen even in Cooomassie stained gels of crude plant extracts. In some samples, IFN is degraded during isolation while in other samples it is protected.
Figure 10B:
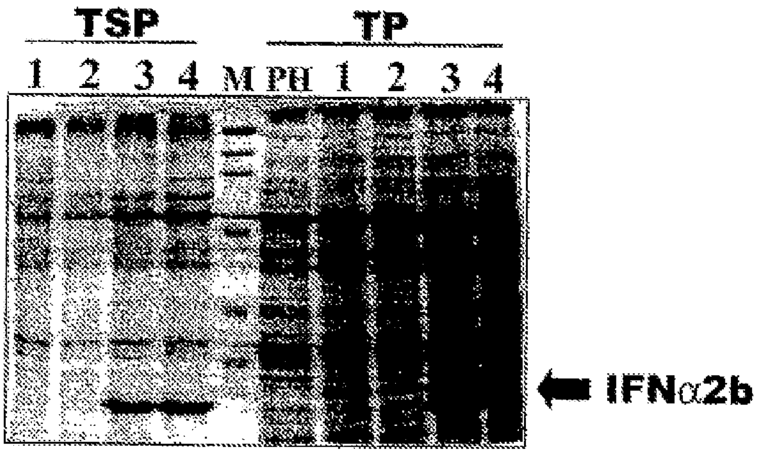

The left and right flanks are the regions in the chloroplast genome that serve as homologous recombination sites for stable integration of transgenes. A strong promoter and the 5' UTR and 3' UTR are necessary for efficient transcription and translation of the transgenes within chloroplasts. For multiple gene expression, a single promoter may regulate the transcription of the operon, and individual ribosome binding sites must be engineered upstream of each coding sequence (2) (FIG. 10). The following steps are used in vector construction:

1. Amplification of flanking sequences of plastid with primers that are designed on the basis of known sequence of the tobacco chloroplast genome (between 16S-23S region of chloroplast).
2. Insert the PCR product containing the flanking sequence of the chloroplast genome into pUC19 plasmid digested with PvuII restriction enzyme (to eliminate the multiple cloning site), dephoshorylated with the help of alkaline phosphatase (CIP) for 5 min at 50° C. (to prevent recircularization of cloning vector). Inactivate CIP enzyme at 68° C. for 10 min.

Clone chloroplast transformation cassette (which is made blunt with the help of T4 DNA polymerase or Kienow filling) into a cloning vector digested at the unique Pvull site in the spacer region, which is conserved in all higher plants examined so far.

Delivery of Foreign Genes into Chloroplasts Via Particle Gun.

This is most successful and a simple technique to deliver transgenes into plastids and is referred as Biolistic PDS-1000/He Particle Delivery System (18,19). This technique has proven to be successful for delivery of foreign DNA to target tissues in a wide variety of plant species and integration of transgenes has been achieved in chloroplast genomes of tobacco (2), *Arabidopsis* (20), potato (21), tomato (25) and transient expression in wheat (22), carrot, marigold and red pepper (23) (see Note 5).

Preparation of Gold Particle Suspension.

1. Suspend 50-60 mg gold particles in 1 mL 100% ethanol and vortex for 2 min.
2. Spin at maximum speed ~10,000×g (using tabletop microcentrifuge) for 3 min.
3. Discard the supernatant.
4. Add 1 ml fresh 70% ethanol and vortex for 1 min.
5. Incubate at room temperature for 15 min and shake intermittently.
6. Spin at 10,000×g for 2 min.
7. Discard supernatant, add 1 ml sterile distilled $H_2O$, vortex for 1 min, leave at room temperature for 1 min, and spin at 10,000×g for 2 min.
8. Repeat above washing process three times with $H_2O$ (step 7).
9. Resuspend the gold-pellet in 1 mL 50% glycerol, store stock in −20° C. freezer.

Precipitation of the Chloroplast Vector on Gold Particles for Five Samples.

1. Take 50 μl of the gold particles in 1.5 mL tube after vortexing for 1 min.
2. Add 10 μl DNA (about 1 μg/μl plasmid DNA), and vortex the mixture for 30 sec.
3. Add 50 μl of 2.5 M $CaCl_2$ and vortex the mixture for 30 sec.
4. Add 20 μl of 0.1 M spermidine and vortex the mixture for 20 min at 4° C.

Washing of Chloroplast Vector Coated on Gold Particles.

1. Add 200 μl 100% ethanol and vortex for 30 sec.
2. Spin at 3000×g for 40 sec.
3. Pour off ethanol supernatant.
4. Repeat ethanol washings five times.
5. In the last step, pour off ethanol carefully and add 35-40 μl ethanol (100%).

Preparation of Macrocarriers.

1. Sterilize macrocarriers by dipping in 100% ethanol for 15 min and insert them into sterile steel ring holder with the help of a plastic cap when air-dried.
2. Vortex the gold-plasmid DNA suspension and pipet 8-10 μl in the center of macrocarrier and let it air dry.

Gene Gun Setup for Bombardment of Samples.

1. Wipe the gun chamber and holders with 100% ethanol using fine tissue paper (do not wipe the door with alcohol).
2. Turn on the vacuum pump.
3. Turn on the valve (Helium pressure regulator) of Helium gas tank (anti-clockwise).
4. Adjust the gauge valve (adjustable valve) 200 to 250 psi above the desired rupture disk pressure (clockwise) using adjustment handle.
5. Turn on the gene gun.
6. Place the rupture disc (sterilized by dipping in 100% ethanol for 5 min) in the rupture disc-retaining cap and tightly screw to the gas acceleration tube.
7. Place a stopping screen in the macrocarrier launch assembly and above that place macrocarrier with gold particles with chloroplast vector facing down towards screen. Screw assembly with a macrocarrier cover lid and insert in the gun chamber.
8. Place an intact leaf or explants to be bombarded on a filter paper (Whatman No. 1) soaked in medium containing no antibiotics. Place sample plate over target plate shelf, insert in the gun chamber and close the bombardment chamber door.
9. Press Vac switch to build pressure (up to 28 inches of Hg) in the vacuum gauge display. Turn same switch down at hold point and press Fire switch until you hear a burst sound of the ruptured disc.
10. Press Vent switch to release the vacuum and open the chamber to remove sample.
11. Shut down the system by closing the main valve (Helium pressure regulator) on the Helium gas cylinder. Create some vacuum in the gene gun chamber and keep using fire switch on and off until both pressure gauges' show zero reading. Release the vacuum pressure and turn off the gene gun and vacuum pump.
12. Incubate bombarded sample plates in the culture room for two days in the dark (i.e. covered with aluminum foil) and on the third day cut explants in appropriate pieces and place on the selection medium.

Plant Tissue Culture and Chloroplast Transformation.

Tobacco Chloroplast Transformation.

A highly efficient and reproducible protocol has been established for *Nicotiana tabacum* cv. Petit Havana (Daniell, H. (1997) *Methods in Mod. Biol. Recombinant gene expression protocols.* 62, 463-489.

1. Bombard 4 weeks old dark green tobacco leaves on the abaxial (bottom side) side with the chloroplast vector and incubate leaves in the dark for 2 days on selection free medium.
2. On the third day cut bombarded leaf explants into small square pieces (5 mm) and place explants facing abaxial surface towards selection medium containing MS salts, 1 mg/l thiamine HCl, 100 mg/l myo-inositol, 3% sucrose, 1 mg/l BAP and 0.1 mg/I IAA along with 500 mg/l spectinomycin as a selective agent.
3. Transgenic shoots should appear after three to five weeks of transformation. Cut the shoot leaves again into small square explants (2 mm) and subject to a second round of selection for achieving homoplasmy on fresh medium.

4. Regenerate transgenic shoots (confirmed by PCR for transgene integration) on rooting medium containing MS salts, 1 mg/l thiamine HCl, 100 mg/l myo-inositol, 2% sucrose and 1 mg/l IBA with 500 mg/l spectinomycin.
5. Transfer transgenic plants into pots under high humidity and move them to green house or growth chamber for further growth and characterization.

Plastid Transformation of Edible Crops.

The concept of universal vector for using the chloroplast DNA from one plant species to transform another species (of unknown sequence) was developed by the Daniell group (8). Using this concept both tomato and potato chloroplast genomes were transformed as described below.

Potato Chloroplast Transformation.

Using the tobacco chloroplast vector, leaf tissues of potato cultivar FL1607 was transformed via biolistics, and stable transgenic plants were recovered using the selective aadA gene marker and the visual green fluorescent protein (GFP) reporter gene (21).

1. Bombard potato leaves (3-4 week old) and incubate in the dark for 2 days on selection free medium.
2. Third day excise leaves into small square pieces (5 mm) and place on MS medium containing BS vitamins, 5 mg/L ZR, 0.1 NAA, and 3% sucrose. Gradually increase spectinomycin selection pressure (40 to 400 mg/L) after every two weeks subculture under diffuse light.
3. Regenerate shoots from transgenic potato calli on MS medium containing BS vitamins, 0.01 mg/L NAA, 0.1 mg/L GA3, 2% sucrose and 40-400 mg/L spectinomycin.
4. Transfer transgenic shoots on basal MS medium containing BS vitamins, 2% sucrose and 40-400 m g/L spectinomycin for root induction. Transfer transgenic plantlets to growth chamber.

Tomato Chloroplast Transformation.

Using the tobacco chloroplast vector, tomato (*Lycopersicon esculentum* cv. IAC Santa Clara) plants with transgenic plastids were generated using very low intensity of light (25).

1. Bombard four-week-old tomato leaves and incubate in the dark for 2 days on selection free medium.
2. Excise bombarded leaves into small pieces and place on shoot induction medium containing 0.2 mg/L IAA, 3 mg/L BAP, 3% sucrose and 300 mg/L spectinomycin.
3. Select spectinomycin-resistant primary calli after a three to four month duration without any shoot induction.
4. Regenerate shoots in about four weeks after transfer of transgenic calli to shoot induction medium containing 0.2 mg/L IAA, 2 mg/L ZR, 2% sucrose and 300 mg/L spectinomycin then root on hormone-free medium. Transfer regenerated transgenic plants into the greenhouse.

Molecular Analysis of Transgenic Plants.

PCR Screening of Transgenic Shoots.

This method has been used to distinguish between mutants, nuclear and chloroplast transgenic plants. By landing one primer on the native chloroplast genome adjacent to the point of integration and a second primer on the aadA gene (26. PCR product of an appropriate size should be generated in chloroplast transformants. Since this PCR product cannot be obtained in nuclear transgenic plants or mutants, the possibility of nuclear integration or mutants should be eliminated.

1) Extract the genomic DNA from transgenic leaf tissue using DNeasy Plant kit (QIAGEN Inc.) by following vender's instructions. For lower amount of transgenic tissues, volume of buffers may be reduced appropriately.
2) Run PCR reaction with Taq DNA Polymerase (QIAGEN Inc.) using appropriate primers following the same conditions as described above for amplification of flanking sequences.

Analysis of Homoplasmy by Southern Blot.

In Southern blot analysis, tobacco plastid genome digested with suitable restriction enzymes should produce a smaller fragment (flanking region only) in wild type plants compared to transgenic chloroplast that include transgene cassette as well as the flanking region. In addition, homoplasmy in transgenic plants is achieved when only the transgenic fragment is observed.

Transfer of DNA to Membrane.

1. Digest the genomic DNA (~2 to 10 μg) with suitable restriction enzymes from transgenic samples (including wild type as a control) and run digested DNA on 0.8% agarose gel containing 5 μL EtBr (from 10 mg/mL stock) in 100 mL for four hours at 40V.
2. Soak gel in 0.25 N HCl (depurination solution) for 15 minutes and rinse gel twice in distilled $H_2O$ for 5 minutes.
3. Soak gel for 20 minutes in transfer buffer to denature DNA.
4. Transfer overnight DNA from gel to nylon membrane (pre-soak first in water, then in transfer buffer for 5 minutes) using the transfer buffer.
5. Next day, rinse membrane twice with 2×SSC buffer for 5 minutes each and air-dry for 5 minutes on filter papers. Cross-link transferred DNA to membrane using GS GeneLinker UV Chamber (Bio-Rad) at appropriate (C3) setting.

Preparation of Probe.

1. Digest any plasmid (containing flanking sequences of the chloroplast genome) with appropriate restriction enzymes.
2. Denature 45 μL flanking DNA fragment (50-250 ng) at 95° C. for 5 minutes, then place on ice for 2-3 minutes.
3. Add denatured probe to Ready-To-Go DNA Labeling Beads (−dCTP) tube (Amersham Biosciences, USA) and gently mix by flicking the tube.
4. Add 5 μL radioactive $\alpha^2P$ (dCTP; Amersham Biosciences, USA) to probe mixture and incubate at 37° C. for 1 hour and filter the probe using ProbeQuant G-50 Micro Columns (Amersham Pharmacia Biotech Inc. USA).

Prehybridization and Hybridization.

Place the blot (DNA transfer side facing towards the solution) in a hybridization bottle and add 10 mL Quik-Hyb (Stratagene, USA).

Incubate for 1 hour at 68° C. Add 100 μL sonicated salmon sperm (10 mg/mL stock; Stratagene, USA) to the labeled probe and heat at 94° C. for 5 minutes and add to bottle containing membrane and Quik-Hyb solution. Incubate for 1 hour at 68° C.

Washing and Autoradiography.

1. Discard Quik-Hyb solution with probe and wash membrane twice in 50 mL (2×SSC buffer and 0.1% SDS) for 15 minutes at room temperature.
2. Wash membrane twice in 50 mL (0.1×SSC buffer and 0.1% SDS) for 15 minutes at 60° C.
3. Wrap the wash membrane in saran wrap and expose blot to x-ray film in the dark and leave at −70° C. until ready for development.

Determination of Transgene Expression by Western Blot.

Extraction of Plant Protein.

1. Grind 100 mg of leaf in liquid nitrogen and add 200 μL of extraction buffer to samples on ice.

2. Add appropriate volume of freshly prepared 2× Sample loading buffer to an aliquot plant extract (from a stock containing 50 μL/3-mercaptoethanol and 950 μL sample loading buffer).
3. Boil samples for 4 minutes with loading dye and centrifuge for 2 minutes at 10,000×g, then immediately load 20 μL samples into gel.

Running Gel.

Load samples on gel and run for half hour at 100 V, then 1 hour at 150 V until the marker bands corresponding to your protein are in middle.

Transfer of Protein to Membrane.

Transfer protein from gel to membrane using Mini Transfer Blot Module at 30 V overnight or 65 V for 2 hours or 100 V for 1 hour. Membrane wrapped in saran wrap can be stored at −20° C. for a few days if necessary.

Membrane Blocking

1. After transfer, rinse membrane with water and incubate membrane in PTM (100 mL 1×PBS, 50 μL 0.05% Tween 20, and 3 g dry milk (3%) for 1 hour at room temperature.
2. Add primary antibody in suitable dilution for 15 mL and incubate for 2 hours at room temperature. Wash membrane twice with 1×PBS for 5 minutes each.
3. Add secondary antibody in proper dilution for 20 mL. Incubate for 1.5 hours at room temperature on a shaker.
4. Wash twice with PT (100 ml 1×PBS+50 μL Tween 20) for 15 minutes and finally with 1×PBS for 10 minutes.

Exposure of the Blot to X-Ray Film.

1. Mix 750 μL of each chemiluminescent solution (Luminol Enhancer and Stable Peroxide) in 1.5 mL tube and add to membrane, cover thoroughly.
2. Wipe out extra solution and expose blot to x-ray film for appropriate duration and develop film.

Seed Sterilization

1. Vortex small amount of seeds into microcentrifuge tube with 1 mL 70% ethanol for 1 minute. Discard ethanol after brief spin.
2. Add 1 mL disinfecting solution (1.5% Bleach and 0.1% Tween 20) in tube and vortex intermittently for 15 min. Discard solution after brief spin.
3. Wash the seed thrice with sterile distilled water.
4. Spray seeds with sterile water on plate containing RMOP basal medium supplemented with 500 μg/mL spectinomycin to determine maternal inheritance in transgenic chloroplast plants.

Evaluation of Results.

Maternal Inheritance in Chloroplast Transgenic Plants.

Transgenes integrated into chloroplast genomes are inherited maternally. This is evident when transgenic seed of tobacco are germinated on RMOP basal medium containing 500 μg/mL spectinomycin. There should be no detrimental effect of the selection agent in transgenic seedlings whereas untransformed seedlings will be affected.

CTB-GM1-Gangliosides Binding ELISA Assay.

1. Coat microtiter plate (96 well ELISA plate) with monosialoganglioside-GMI {3.0 μg/mL in bicarbonate buffer (15 mM $Na_2CO_3$, 35 mM $NaHCO_3$, pH 9.6)} and as a control, coat BSA (3.0 ug/mL in bicarbonate buffer) in few wells.
2. Incubate plate overnight at 4° C.
3. Block wells with 1% (w/v) bovine serum albumin (BSA) in 0.01 M phosphate-buffered saline (PBS) for two hours at 37° C.
4. Wash wells thrice with PBST buffer (PBS containing 0.05% Tween 20).
5. Incubate plate by adding soluble protein from transformed and untransformed plants and bacterial CTB in PBS.
6. Add primary antibodies (rabbit anti cholera serum diluted 1:8000 in 0.01 M PBST containing 0.5% BSA) and incubate plate for 2 hours at 37° C.
7. Wash well thrice with PBST buffer.
8. Add secondary antibodies diluted 1:50,000 (mouse anti rabbit IgG-alkaline phosphatase conjugate in 0.01 M PBST containing 0.5% BSA) and incubate plate for 2 hours at 37° C.
9. Develop plate with Sigma Fast pNPP substrate. Stop reaction by adding 3 M NaOH and read plate absorbance at 405 nm.

The macrophage lysis assay is as follows:

1. Isolate crude extract protein from 100 mg transgenic leaf using 200 μL of extraction buffer containing CHAPS detergent (4% CHAP, 10 mM EDTA, 100 mM NaCl, 200 mM Tris-HCl, pH 8.0, 400 mM sucrose, 14 mM β-mercaptoethanol, 2 mM PMSF) and one without CHAPS detergent.
2. Spin samples for five minutes at 10,000×g and use both supernatant and homogenate for assay
3. Plate macrophage cells RAW 264.7 (grown to 50% confluence) into 96-wells plate, incubated in 120 μL Dulbecco's Modified Eagle's Medium (DMEM; from Invitrogen life technologies).
4. Aspirate medium from wells and add 100 μL medium containing 250 ng/mL proteins in crude leaf extract.
5. In control plate, add only DMEM with no leaf fraction to test toxicity of plant material and buffers.
6. In another plate, add 40 μL dilutions onto RAW 264.7 cells from plant samples, which serially diluted 2 fold, so that the top row had plant extract at 1:14 dilution.
7. Add 20 μL of MIT 3-[4,5-dimethylthiazol-2-yl]-2,5-diphenyltetrazolium bromide; Sigma) to each well containing cells (from a stock 5 mg/ml MTT dissolved in 1×PBS and filter sterilize) after 5 hours to assess the cell death.
8. Incubate the plate at 37° C. for 5 hours. Remove media with needle and syringe. Add 200 μL of DMSO to each well and pipette up and down to dissolve crystals. Transfer to plate reader and measure absorbance at 550 nm.

Active PA was found in both the supernatant and homogenate fractions. However, maximum macrophage lysis activity was noticed in supernatant when extraction buffer was used with CHAPS detergent.

Cholera Toxin (CTB) Antigen as an Edible Vaccine.

Figure 11:
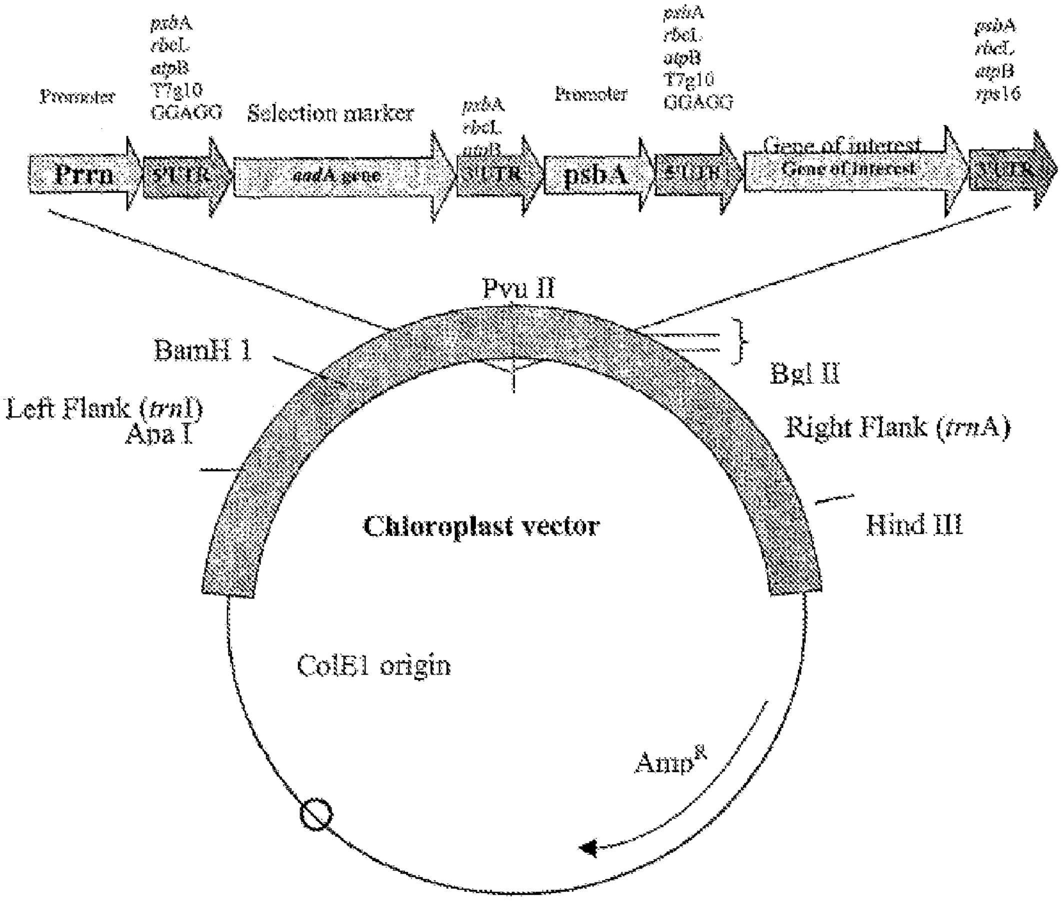
FIG. 11 shows a generalized schematic view of a plastid transformation vector.

Chloroplast transgenic plants are ideal for production of vaccines. The heat labile toxin B subunits of *E. coli* enterotoxin (LTB), or cholera toxin of *Vibrio cholerae* (CTB) have been considered as potential candidates for vaccine antigens. Integration of the unmodified native CTB gene into the chloroplast genome has demonstrated high levels of CTB accumulation in transgenic chloroplasts (Daniell, H., et al. (2001). *J. Mol. Biol.* 311, 1001-1009.). This new approach not only allowed the high level expression of native CTB gene but also enabled the multimeric proteins to be assembled properly in the chloroplast, which is essential because of the critical role of quaternary structure for the function of many vaccine antigens. The expression level of CTB in transgenic plants was between 3.5% and 4.1% tsp and the functionality of the protein was demonstrated by binding aggregates of assembled pentamers in plant extracts similar to purified bacterial antigen, and binding assays confirmed that both chloroplast-synthesized and bacterial CTB bind to the intestinal membrane GM1-ganglioside receptor, confirming correct folding and disulfide bond formation of CTB pentamers within transgenic chloroplasts (FIG. 11).

Oral Delivery of Vaccines and Selection of Transgenic Plants without the Use of Antibiotic Selectable Markers.

Betaine aldehyde dehydrogenase (BADH) gene from spinach has been used as a selectable marker to transform the chloroplast genome of tobacco (Daniell, H. et al., (2001) *Curr. Genet.* 39, 109-116). Transgenic plants were selected on media containing betaine aldehyde (BA). Transgenic chloroplasts carrying BADH activity convert toxic BA to the beneficial glycine betaine (GB). Tobacco leaves bombarded with a construct containing both aadA and BADH genes showed very dramatic differences in the efficiency of shoot regeneration. Transformation and regeneration was 25% more efficient with BA selection, and plant propagation was more rapid on BA in comparison to spectinomycin. Chloroplast transgenic plants showed 15 to 18 fold higher BADH activity at different developmental stages than untransformed controls. Expression of high BADH level and resultant accumulation of glycine betaine did not result in any pleiotropic effects and transgenic plants were morphologically normal and set seeds as untransformed control plants.

Production of Human Therapeutic Proteins in Transgenic Chloroplasts.

Human Serum Albumin (HSA) Protein.

Human Serum Albumin (HSA) accounts for 60% of the total protein in blood and widely used in a number of human therapies. Chloroplast transgenic plants were generated expressing HSA (Fernandez-San Millan et al., (2003) *Plant Biotechnol. J.* 1, 71-79). Levels of HSA expression in chloroplast transgenic plants was achieved up to 11.1% tsp. Formation of HSA inclusion bodies within transgenic chloroplasts was advantageous for purification of protein. Inclusion bodies were precipitated by centrifugation and separated easily from the majority of cellular proteins present in the soluble fraction with a single centrifugation step. Purification of inclusion bodies by centrifugation may eliminate the need for expensive affinity columns or chromatographic techniques.

Purification of HSA.

1. Solubilize the HSA inclusion bodies from transformed tissues using extraction buffer containing 0.2M NaCl, 25 mM Tris-HCl (pH 7.4), 2 mM PMSF and 0.1% Triton X-100.
2. Spin at 10,000×g. Suspend the pellet in buffer containing 6M Gu-HCl, 0.1M PMS and 0.25 mM Tris-HCl (pH 7.4).
3. Dilute plant extract 100-fold in buffer containing 100 mM NaCl, 50 mM Tris-HCl (pH 8.5) and 1 mM EDTA.
4. Concentrate HSA protein by precipitation using a polyethylenglycol treatment at 37%.
5. Separate protein fractions by running a SDS-PAGE gel and stain gel with silver regent following vender's instruction (Bio-Rad, USA).

Electron Microscopy and Immunogold Labeling.

1. Cut the transformed and untransformed leaf in 1-3 mm squares.
2. Fix them in 0.1 M cacodylate buffer pH 7.4 (2.5% glutaraldehyde, 2% paraformaldehyde and 5 mM $CaCl_2$) for 15 minutes under vacuum and 12 hours at 4° C.
3. Rinse samples twice in 0.1M cacodylate buffer (pH 7.4) after fixation.
4. Dehydrate fixed samples through a graded ethanol series to 95%, then implant in LRW resin at 60° C. for 24 hours.
5. Cut ultra-thin sections using a Leica Ultracut T ultramicrotome and collect sections onto nickel grids.
6. Incubate sections in 0.05M glycine prepared in PBS buffer for 15 minutes to inactivate residual aldehyde groups.
7. Place grids onto drops of blocking solution (PBS containing 2% non-fat dry milk) and incubate for 30 minutes
8. Incubate sections for 1 hour in a goat anti-human albumin polyclonal antibody (dilution range from 1:1000 to 1:10,000 in blocking solution).
9. Wash sections with blocking solution 6×5 minutes each.
10. Incubate sections for 2 hours with a rabbit anti-goat IgG secondary antibody conjugate to 10 nm gold diluted 1:40 in blocking solution.
11. Wash sections 6×5 minutes in blocking solution and 3×5 minutes with PBS, and fixed sections in 2% glutaraldehyde diluted in PBS for 5 minutes.
12. Wash fixed sections in PBS 3×5 minutes, then in distilled water 5×2 min each.
13. Stain sections using uranyl acetate and lead citrate and examine samples under transmission electron microscope at 60 kv.

Notes

1. Gold particles suspended in 50% glycerol may be stored for several months at −20° C. Avoid refreezing and thawing spermidine stock; use once after thawing and discard the remaining solution. Use freshly prepared $CaCl_2$ solution after filter sterilization. Do not autoclave.
2. Precipitation efficiency of DNA on gold and spreading of DNA-gold particles mixture on macrocarriers is very important. For high transformation efficiency via biolistics, a thick film of gold particles should appear on macrocarrier disks after alcohol evaporation. Scattered or poor gold precipitation reduces the transformation efficiency.
3. Generally, a 1000 bp flanking sequence region on each side of the expression cassette is adequate to facilitate stable integration of transgenes.
4. Use of the 5' untranslated region (5' UTR) and the 3' untranslated region (3' UTR) regulatory signals are necessary for higher levels of transgene expression in plastids (13). The expression of transgene in the plant chloroplast depends on a functional promoter, stable mRNA, efficient ribosomal binding sites; efficient translation is determined by the 5' and 3' untranslated regions (UTR). Chloroplast transformation elements Prrn, psbA5'UTR, 3'UTR can be amplified from tobacco chloroplast genome.
5. Bombarded leaves after two-days dark incubation should be excised in small square pieces (5-7 mm) for first round of selection and regenerated transgenic shoots should be excised into small square pieces (2-4 mm) for a second round of selection.
6. Temperature for plant growth chamber should be around 26-28° C. for appropriate growth of tobacco, potato and tomato tissue culture. Initial transgenic shoot induction in potato and tomato require diffuse light. However, higher intensity is not harmful for tobacco.
7. Transformation efficiency is very poor for both potato and tomato cultivars compared to tobacco.
8. Tobacco chloroplast vector gives low frequency of transformation if used for other plant species. For example, when *petunia* chloroplast flanking sequences were used to transform the tobacco chloroplast genome (DeGray, G. et al., (2001), *Plant Physiol.* 127, 852-862.), it resulted in very low transformation efficiency.

Under diffuse light conditions, highly regenerating tomato cultivar (Microtom) shoots produce premature flowering that inhibit further growth of transgenic plants. Therefore, after the first shoot induction phase, shoots should be moved to normal light conditions.

ILLUSTRATIVE EXAMPLE

Reference will now be made in detail to aspects of the invention, which, together with the following example, serve to explain the principles of the invention. The following example is intended as a non-limiting example, and is no way intended as a limitation.

This non-limiting example shows integration of a recombinant IFNα2b containing a polyhistidine purification tag as well as a thrombin cleavage site into the chloroplast genome of a low-nicotine tobacco variety (LAMD-609) which could be used for animal studies. Homoplasmy was achieved in the $T_0$ generation as determined by Southern blot. Western blots detected monomeric and multimeric forms of IFNα2b using interferon alpha monoclonal antibody. ELISAs were used to quantify up to 12.5% of total soluble protein in LAMD-609 leaf tissues. Two different bioassays confirm that the expressed transgene is functioning as well as the human-drug counterpart Chloroplast vectors: PCR was used to generate a 700 bp IFNα2b gene cassette (HIS/THR/IFNα2b) containing both a thrombin cleavage site and a polyhistidine tag at the 5' end and a Notl restrictions site at the 3' end to subclone into the universal chloroplast expression vector, pLD-CtV (5.9 kb). The resulting vector, pLD-RF-IFNα 2b (6.6 kb, see FIG. 1) was used to transform tobacco chloroplasts. The trnl and trnA genes were used as flanking sequences for homologous recombination to insert the IFNα2b containing cassette into the spacer region between the these two tRNA genes in the inverted repeat region of the chloroplast genome, as reported previously. The constitutive 16s rRNA promoter, which can be recognized by both the chloroplast encoded RNA polymerase and the nuclear encoded RNA polymerase, was used to drive transcription. The aadA gene conferring spectinomycin resistance was used for selection of transgenic shoots. The IFNα2b gene coding for recombinant IFNα2b was regulated by the psbA 5' and 3' elements. The 5'UTR from psbA, including its promoter, was used for transcription and translation enhancement and the 3'UTR region conferred transcript stability.

Since oral delivery of IFNα2b is highly desired, the above IFNα2b gene cassette was integrated into two different varieties of tobacco: Petit Havana (model) and a low-nicotine hybrid tobacco called LAMD-609, which could be used to test oral delivery of IFNα2b in animal studies. Also, it is inserted into the carrot plastid transformation vectors.

Transgene integration into the chloroplast genome by PCR analysis: Chloroplast transgenic lines were generated by particle bombardment as described previously. After bombarding *Nicotiana tabacum* cv. Petit Havana and LAMD-609 tobacco leaves with the chloroplast vector, the leaves were grown on selective medium containing 5 μg/ml and 300 μg/ml spectinomycin, respectively. For Petit Havana two primer sets were used to identify transgenic lines. For the 3P/3M set, the 3P primer annealed to the chloroplast genome outside of the inserted cassette and the 3M primer annealed to the chimeric aadA (see FIG. 1). When both primers annealed, a 1.65 kb PCR product was observed, however, there was no PCR product in the untransformed (−) Petit Havana line. No PCR product should be observed if the foreign gene cassette was integrated into the nuclear genome or if the plants were mutants lacking the aadA gene. Out of the 6 putative transgenic lines shown, 5 were positive for insertion of the foreign cassette. For the 5P/2M set, the SP primer annealed to the chimeric aadA gene and the 2P primer annealed to the trnA gene within the cassette. When both of the primers annealed, a 2.3 kb PCR product was observed, however, there was no PCR product in the untransformed (−) Petit Havana line. The correct size of PCR product (2.3 kb) indicated that the entire foreign gene cassette and not just the aadA gene had been integrated into the chloroplast genome. For the LAMD-609, two primer sets were used to identify transgenic lines (see FIG. 2). All of the putative LAMD-609 transgenic lines shown were positive for insertion of the foreign gene cassette.

Figures 3A, 3B:
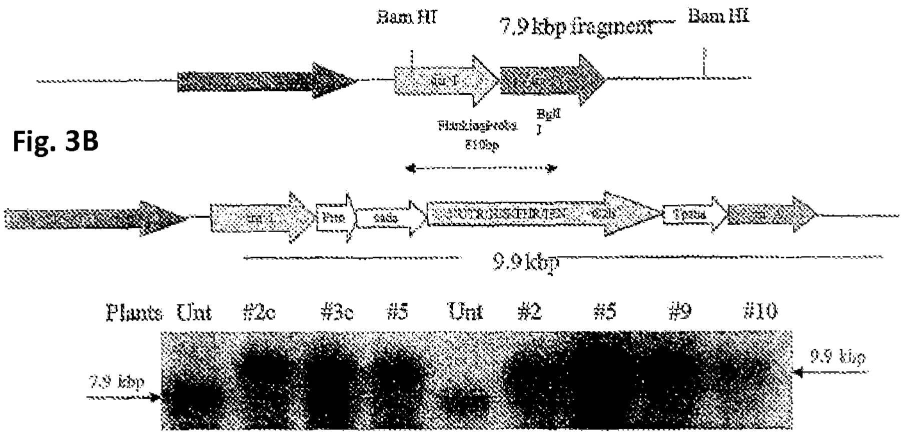
FIG. 3A-FIG. 3B shows a Southern blot for confirmation of chloroplast integration and determination of homoplasmy/heteroplasmy in $T_0$ of both tobacco varieties.

Chloroplast integration of transgenes and homoplasmy: Southern blots were done to further verify that the transgenes had been integrated into the chloroplast genome and to detennine homoplasmy (containing only transformed chloroplast genomes) or heteroplasmy (containing both transformed and untransformed chloroplast genomes). Total plant DNA from transformed plants was digested with the enzyme BamHI which generated a 9.9-kb when probed with the 0.81 kb probe that hybridizes to the trnl and trnA flanking sequences (see FIG. 3). Pg 65. Untransformed plant DNA from both tobacco varieties generated only a 7.9 kb fragment, indicating no integration of foreign DNA. Transgenic plant DNA ($T_0$) generated only the 9.9 kb fragment in all but one, indicating homoplasmy (contained only transformed chloroplast genomes). Note that in plant #3c, two fragments indicate heteroplasmy (presence of both untransformed and transformed chloroplast genomes). Attainment of homoplasmy in the transformants provides an estimate of the integrated transgene copy number of approximately 10,000 copies per tobacco leaf cell and indicates that homoplasmy can be achieved in the $T_0$ generation (first generation of a transgenic line).

Figure 4A:
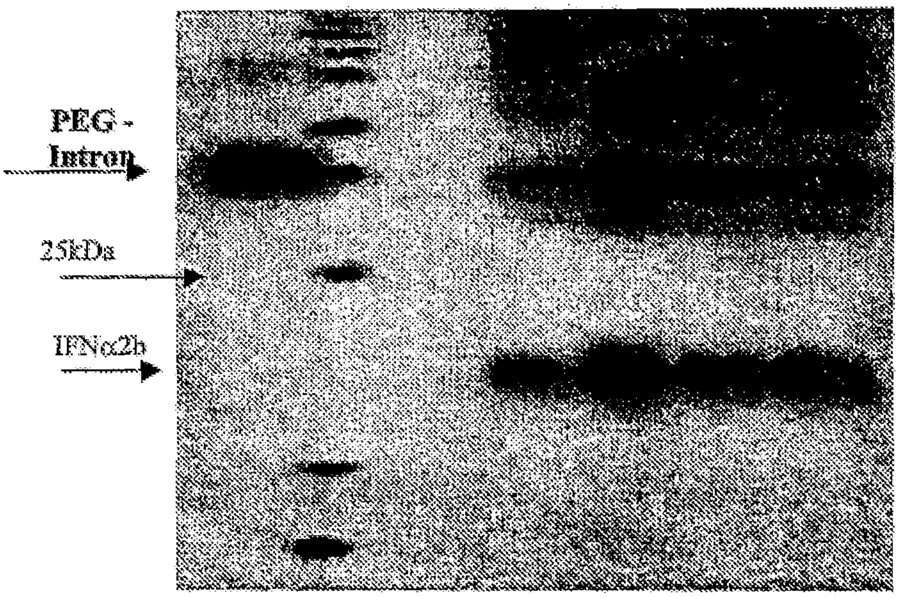
FIG. 4(A)-FIG. 4(B) show a Western blot of LAMD-609 transgenic chloroplast expressing IFNα2b.
Figure 4B:
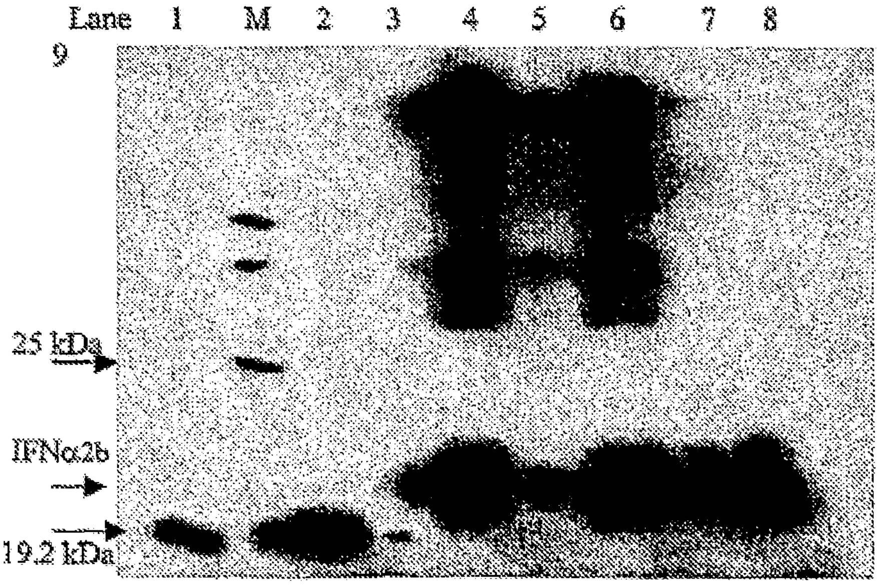
Figure 5A:
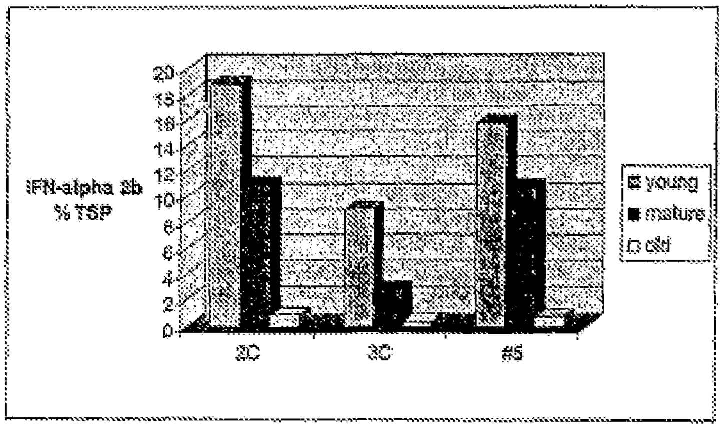
FIG. 5(A)-FIG. 5(B) shows graphical quantification of IFNα2b in transgenic chloroplasts of To generation.
Figure 5B:
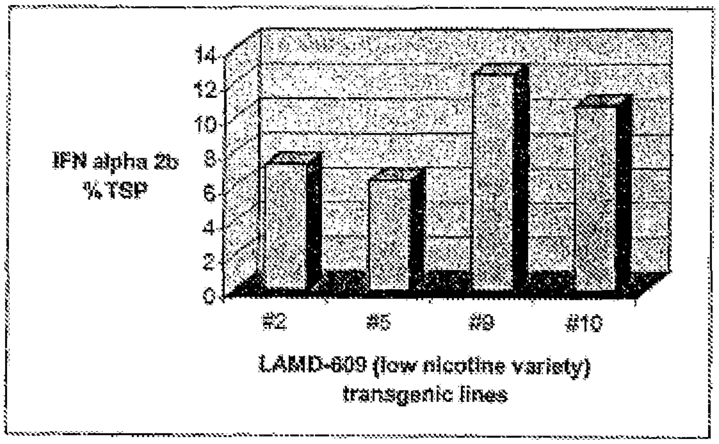

IFNα2b expression in transgenic chloroplasts: Western blots were performed on leaf extracts of transgenic lines for both varieties of tobacco. The total plant protein was separated using 15% SDS-PAGE. The HIS/THR/IFNα2b protein was detected by mouse MAB against human IFNα. For LAMD-609, western blots detected monomers and multimers of HIS/THR/IFNα2b protein at approximately 21.5 kDa, which is smaller than the PEG-Intron™ standard at approximately 32 kDa (see FIG. 4). For Petit Havana, western blots detected monomers and multimers of IIIS/THR/IFNα2b protein at approximately 21.5 kDa, which is slightly larger than 19.2 kDa of the Futron® A standard (see FIG. 5).

Quantification of IFNα2b in transgenic chloroplasts: To quantify the amount of IFNα2b in transgenic Petit Havana and LAMD-609 leaf extracts, an indirect enzyme-linked immunosorbent assay (ELISA) was used. The currently marketed drug called PEG-Intron™ (recombinant IFNcx2b conjugated to monomethoxy polyethylene glycol) manufactured by the Schering Corporation was used to make an eight-point standard curve. Plant protein extracts were diluted into various volumes of coating buffer to determine the dilution that would be in the linear range of PEG-Intron™ standard curve. The primary antibody was Mouse Monoclonal Antibody Against Human futerferon (MMHA-2). The secondary antibody was Goat anti-mouse IgG conjugated to horseradish peroxidase. The addition of One Step Substrate (TMB) into the wells resulted in a color change that was eventually read on a Bio-Tek Instrument plate reader with a 450 nm filter.

The total soluble protein (tsp) in the plant leaf extracts was determined with a Bradford Bio-Rad Protein Assay. The levels of IFNα2b in transgenic Petit Havana and LAMD-609 were calculated as a percentage of the total soluble protein of leaf extracts. The IFNα2b concentration (ng/μl) was divided by the tsp (ng/μl) and then multiplied by 100 to give a percentage (see FIG. 6). The highest amount of soluble IFNα2b was observed in the young leaves, probably because of low level of protease. The transgenic line with the lowest expression of IFNα2b was heteroplasmic (see FIGS. 5&6) therefore, the level of expression corresponded to the levels of homoplasmy or heteroplasmy. Different levels of expression among $T_0$ transgenic lines are not uncommon due to heteroplasmy or other physiological conditions. The quantity of IFNα2b produced in chloroplasts was up to 18.8% of total soluble protein in Petit Havana and up to 12.5% in LAMD-609. The T1 generation transgenic lines showed up to 27% IFNα2b in the total protein. The protein was expressed in such large amounts that it could be seen in Cooomassie gels even in crude plant extracts. Because majority of IFNα2b is seen in the total protein and not in the supernatant, this allows easy purification and protection from proteolytic degradation. Northern blots show that IFNα2b is transcribed quite efficiently in chloroplast transgenic lines. These expression levels are more than adequate for either histidine-tag purification or for use in oral IFNα2b delivery for animal or clinical studies.

As shown above, any and all interferons may be expressed in transgenic chloroplasts without any fusion proteins or with fusion proteins as desired for purification and stability.

Study of Bioactivity of IFNα2b from Transgenic Tobacco Plants

Production of Tobacco Plant Extracts

Figure 1B:
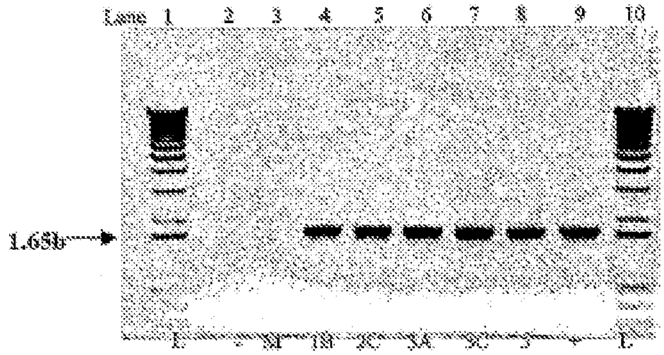
Figure 1C:
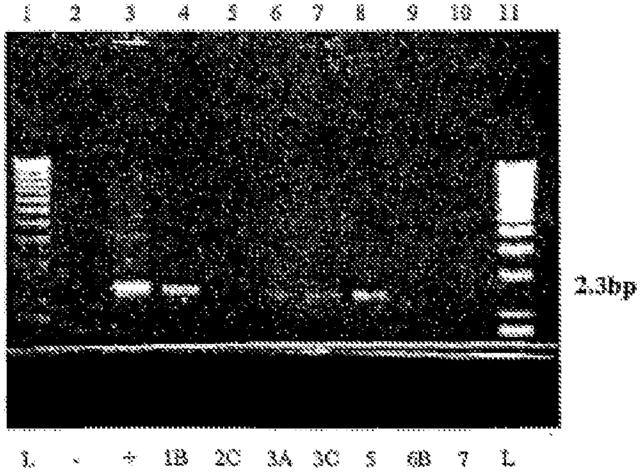
Figure 2A:
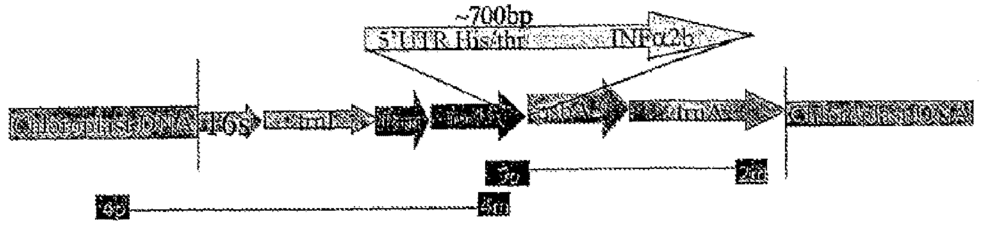
FIG. 2(A)-FIG. 2(C) show the pLD-RF-IFNα2b vector and PCR Analysis of Putative LAMD-609 Transgenic Lines.
Figure 2B:
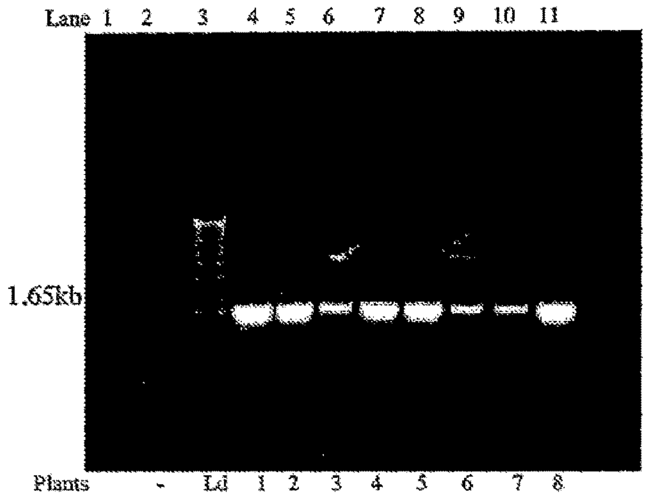
Figure 2C:
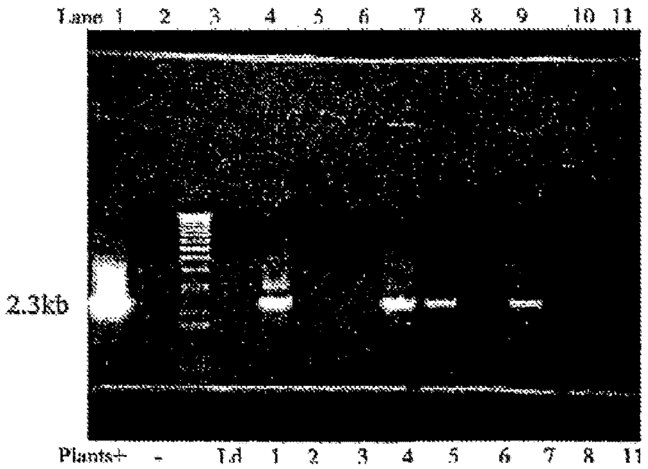

Leaves of IFNα2b transgenic tobacco plants were collected and frozen in aliquots at −80° C. After that, one aliquot was pulverized in liquid nitrogen and 0.1 gram of dry weight of plant was homogenized in 400 μl of extraction buffer (15 mM $Na2CO_3$, 35 mM $NaHCO_3$, 3 mM $NaN_3$, 0.1% Tween 20, pH:9.6). The homogenate was centrifuged at 6000×g to eliminate cell debris. The soluble part was tested for IFNα by western-blot. Also, as a negative control, we performed the same extraction protocol for non-transgenic tobacco plants. As shown in FIG. 1, IFNα2 transgenic tobacco plant extract was positive for IFNα.

The above procedure is for extraction of total soluble protein. The amount of IFNα2 in this extract was quantified by comparing, in western-blot, the IFNα2 band from transgenic plants with the commercial IFNα2 band (Intron A, Shering-Plough). Intron A is a solution of purified IFNα2b at 75 μg mL.

Bioactivity of IFNα2 from Transgenic Tobacco Plant Extracts

The method to determine IFNα2 activity is based on its antiviral properties. The procedure measures the ability of IFNα to protect HeLa cells against the cytopathic effect of encephalomyocarditis virus (EMC). The assay was performed in a 96-well microtiter plate. First, $2\times10^4$ HeLa cells were seeded per well in 150 μL of medium containing serial IFNα. dilutions and incubated for 24 hours. $10^5$ PFU of EMC virus was added per well and 24 hours later the cytopathic effect was measured as follows. Medium was removed, wells were rinsed twice with PBS and stained with methyl violet dye solution and the optical density was read at 540 nm. The values of optical density are proportional to the antiviral activity of IFNα. The activity of IFNα2 from transgenic plants was compared with that of commercial IFNα2 (Intron A). In parallel possible toxicity was tested as was the possible antiviral effect of tobacco plant extract in the previous bioassay. The toxicity of tobacco plants against HeLa cells, was determined incubating the same serial dilutions of IFNα2 transgenic plant extracts with HeLa cells, but without adding EMC virus. The antiviral effect for other possible components of tobacco plants was tested by incubating serial dilutions of non-transgenic tobacco plant extract with HeLa cells and adding EMC virus.

Figure 6:
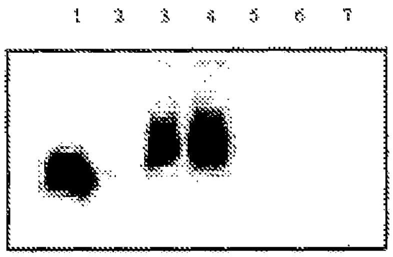
FIG. 6 shows that IFNα2 transgenic tobacco plant extract was positive for IFNα.

The viability of HeLa cells with IFNαa2 transgenic plants extracts was 100% when we did not add EMC virus, indicating that the dilutions of IFNα2 transgenic plants extracts tested are not toxic for HeLa cells. In the same way, no antiviral effect of non-transgenic tobacco plant extract was observed when it was incubated with HeLa cells infected by EMV virus. As shown in FIG. 6, we observed that IFNα2 from transgenic tobacco plant extracts was as active as Inton A.

Figure 7:
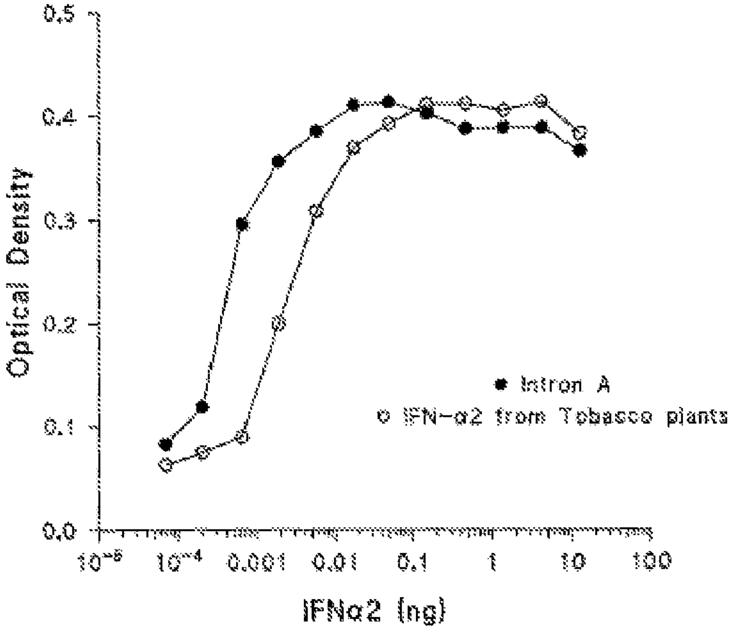
FIG. 7 shows that that IFNα2 from transgenic tobacco plant extracts was as active as Inton A.
Figures 8A, 8B:
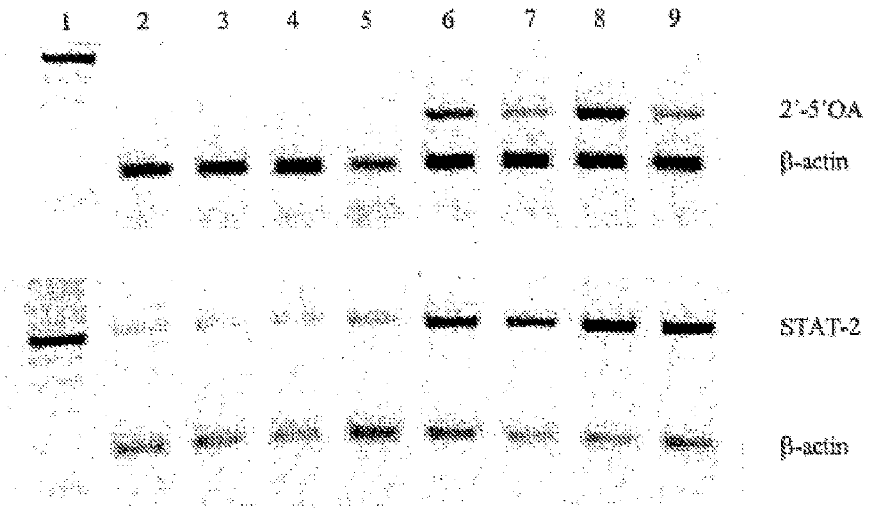
FIG. 8(A)-FIG. 8(B) shows the IFNα2 transgenic tobacco plant extract induced the expression of both 2'=5' OA and STAT-2 mRNAs. Lane 1 shows the molecular weight; 2-3 uninduced HeLA cells; 4-5 show HeLa cells plus non-transgenic tobacco plant extracts; lanes 6-7 shows HeLa cells plus intron A; and lanes 8-9 shows HeLa cells plus IFNα2 transgenic tobacco plant extracts.
Figure 9A:
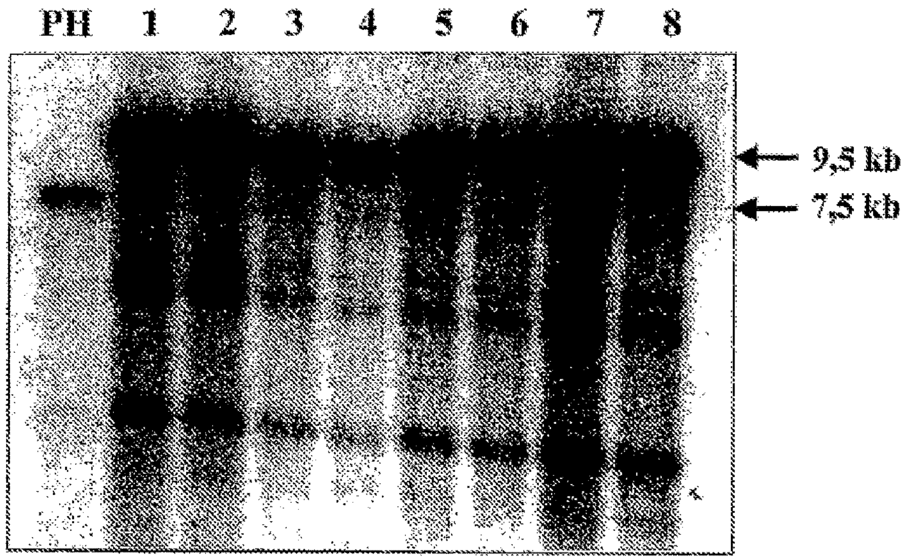
FIG. 9(A)-FIG. 9(B) shows a southern blot demonstrating the expression of IFNα2b in transgenic plants. More specifically, they illustrate Southern blot with transgenic lines expressing high levels of IFN in black and low levels in red. Probe: Flanking sequence.
Figure 9B:
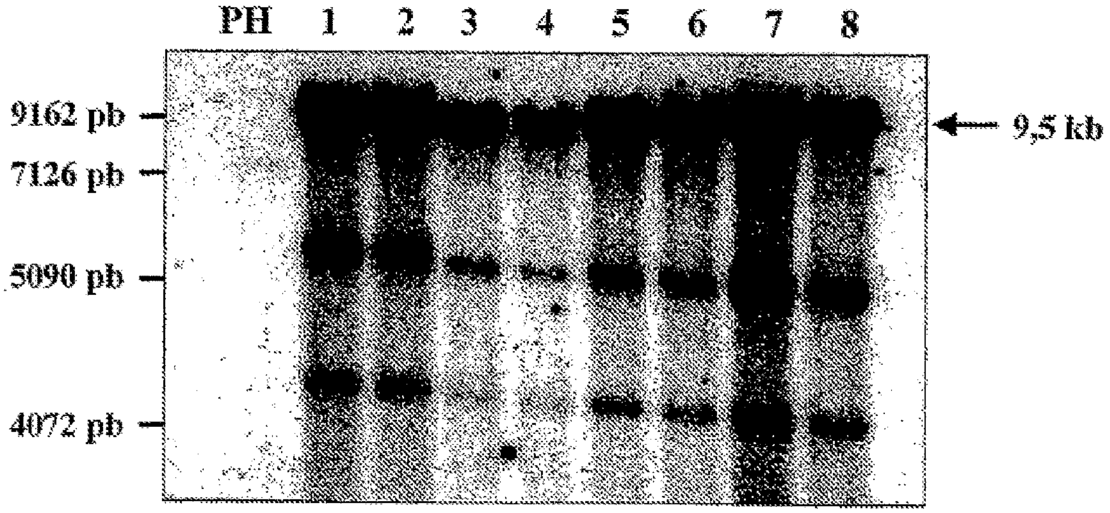

Also, the IFNα activity was tested by measuring the mRNA levels of two genes directly induced by IFNα: 2'-5'oligoadenylate synthetase (2'-5'OA) and STAT-2. For such a study, $0.4\times10^6$ HeLa cells were seeded in sterile six-well plate and incubated overnight. At this time, 37 ng/mL of intron A or IFNα2 from transgenic tobacco plants was added. Five hours later, HeLa cells were removed and total RNA was extracted following the Ultraspec protocol, which is based on the method described by Chomczynski and Sachi. The mRNA levels of 2'-5'OA and Stat-2 are measured by RT-PCR using specific primers for each gene. β-actin was used as internal control. As shown in FIG. 7, IFNα2 transgenic tobacco plant extract induced the expression of both 2'-5'OA and STAT-2 mRNAs.

The aforementioned bioactivity results allowed the following conclusion:

IFNα2 transgenic tobacco plants produce IFNα2; the IFNα2 produced by transgenic tobacco plants is bioactive; and the bioactivity of IFNα2 produced by transgenic tobacco plants is similar to commercial IFNα2 (Intron A).

Expression of Interferon α2b in Transgenic Chloroplasts and Study of Functionality A recombinant IFNα2b containing a polyhistidine purification tag, as well as, a thrombin cleavage site was ligated into a universal chloroplast expression vector that uses trnl and trnA genes (chloroplast transfer RNAs coding for isoleucine and alanine) from the inverted repeat region of the tobacco chloroplast genome as flanking sequences for homologous recombination. The resulting vector, pLD-RF-IFNα2b, was bombarded into Petit Havana and a low-nicotine variety of tobacco, LAMD-609. The His/Thr/IFNα2b cassette was integrated into the chloroplast genome of both varieties of tobacco. Western blots detected monomer and multimeric forms of IFNα2b using interferon alpha monoclonal antibody (MAB). Southern blots confirmed stable, site-specific integration of transgenes into chloroplast genomes and determined homoplasmy or heteroplasmy in the $T_0$ generation. In the Petit Havana transgenic lines, homoplasmy of chloroplast genomes occurs in the first generation and this corresponds to the highest level of IFNα2b expression. ELISAs were used to quantify up to 18.8% of total soluble protein in Petit Havana and up to 12.5% in LAMD-609. These expression levels are more than adequate for either histidine-tag purification or for use in oral IFNα2b delivery for animal or clinical studies.

The method to determine IFNα2 activity is based on its antiviral properties. The procedure measures the ability of IFNα to protect HeLa cells against the cytopathic effect of encephalomyocarditis virus (EMC). We observed that IFNα2 from transgenic tobacco plant extracts was as active as commercially produced Inton A. Also, the IFNα2 activity was tested by measuring the mRNA levels of two genes directly induced by IFNα2: 2'-5'oligoadenylate synthetase (2'-5'OA) and STAT-2. The mRNA levels of 2'-5'OA and Stat-2 were measured by RT-PCR using specific primers for each gene. β-actin was used as internal control. IFNα2 transgenic tobacco plant extract induced the expression of both 2'-5'OA and STAT-2 mRNAs. Therefore, transgenic tobacco chloroplasts produced large amounts on interferon and interferon was fully active and functional.

As is understood in the art any of a number of interferons are suitable for use in this invention. For purposes of illustration a non limiting list of interferons, which have been fully characterized in the art, is provided.

A number of Human interferon genes are also described in J. Interferon Res. 13:443-444(1993).

Table 1 shows an exemplary list of interferon genes, and their specific descriptions.

TABLE 1

| Accession ID | Left Marker | Right Marker | Max Het. | Name |
|---|---|---|---|---|
| GDB: 223545 | 1Q22 | 1q22 | | 1FI16<br>1FNGIP1<br>interferon, gamma-inducible protein 16 |
| GDB: 120620 | 10q23 | 10q24 | 0.0768 | 1FIT1<br>1FI56<br>interferon-induced protein with tetratricopeptide repeats 1<br>Hs.85121<br>G10P1<br>IFNAI1<br>IFI-56<br>interferon-induced protein 56<br>GARG-16<br>Hs.20315 |
| GDB: 119328 | 9p22 | 9p22 | 0.7200 | IFN1@<br>IFNA<br>interferon, type 1, cluster<br>IFN1@ |
| GDB: 13635 | 9p22 | 9p22 | | IFNA1<br>Hs.37026<br>interferon, alpha 1 |
| GDB: 136354 | 9p22 | 9p22 | | IFNA10<br>Hs.1510<br>interferon, alpha 10 |
| GDB: 136355 | 9p22 | 9p22 | | IFNA13<br>interferon, alpha 13 |
| GDB: 136356 | 9p22 | 9p22 | | IFNA14<br>Hs.93907<br>interferon, alpha 14 |
| GDB: 136357 | 9p22 | 9p22 | | IFNA16<br>Hs.56303<br>interferon, alpha 16 |
| GDB: 136358 | 9p22 | 9p22 | | IFNA17<br>interferon, alpha 17 |
| GDB: 136359 | 9p22 | 9p22 | | IFNA2<br>Hs.1739<br>interferon, alpha 2 |
| GDB: 136360 | 9p22 | 9p22 | | IFNA21<br>Hs.836<br>interferon, alpha 21 |
| GDB: 136361 | 9p22 | 9p22 | | IFNA4<br>interferon, alpha 4 |
| GDB: 136362 | 9p22 | 9p22 | | IFNA5<br>interferon, alpha 5 |
| GDB: 136363 | 9p22 | 9p22 | | INFA6<br>interferon, alpha 6 |
| GDB: 136364 | 9p22 | 9p22 | | IFNA7<br>interferon, alpha 7 |
| GDB: 136365 | 9p22 | 9p22 | | IFNA8<br>Hs.73890<br>interferon, alpha 8 |
| GDB: 136366 | 9p22 | 9p22 | | IFNAP22<br>interferon, alpha pseudongene 22 |
| GDB: 120078 | 21q223.1<br>21q22.11 | 21q22.1<br>21q22.11 | 0.8300 | IFNAR1<br>interferon (alpha, beta and omega) receptor 1<br>IFRC<br>IFNAR<br>Hs.1513<br>INTERFERON-ALPHA/BETA RECEPTOR ALPHA CHAIN PRECURSOR |
| GDB: 568494 | 21q22.1<br>21q22.11 | 21q22.1<br>21q22.11 | | IFNAR2<br>interferon (alpha, beta and omega) receptor 2<br>Hs.86958<br>IFNABR |
| GDB: 120522 | 9p22<br>9p21 | 9p22<br>9p21 | | EFNB1<br>Hs.93179<br>IFNB<br>interferon, beta 1, fibroblast<br>Hs.835<br>Hs.93171<br>Hs.93177 |
| GDB: 120079 | 8pter | 9qter | | IFNB3<br>interferon, beta 3, fibroblast |

TABLE 1-continued

| Accession ID | Left Marker | Right Marker | Max Het. | Name |
|---|---|---|---|---|
| GDB: 119329 | 12q14 | 12q14 | 0.7068 | IFNG |
| | 12q24.1 | 12q24.1 | | interferon, gamma |
| | 12q15 | 12q15 | | Hs.856 |
| GDB: 120688 | 6q23 | 6q24 | | IFNGR1 |
| | 6q24.1 | 6q24.2 | | IFNGR |
| | | | | interferon gamma receptor 1 |
| GDB: 142306 | 21pter | 21qter | | IFNGR2 |
| | 21q22.1 | 21q22.1 | | IFNGT1 |
| | 21q22.11 | 21q22.11 | | interferon gamma receptor 2 (interferon gamma transducer 1) |
| GDB: 136367 | | | | IFNP11 |
| | | | | interferon pseudogene 11 |
| GDB: 136368 | | | | IFNP12 |
| | | | | interferon pseudogene 12 |
| GDB: 136369 | | | | IFNP20 |
| | | | | interferon pseudogene 20 |
| GDB: 136370 | | | | IFNP23 |
| | | | | interferon pseudogene 23 |
| GDB: 385667 | 9p22 | 9p22 | | IFNP24 |
| | | | | interferon pseudogene 24 |
| GDB: 119330 | 16pter | 16qter | | IFNR |
| | | | | inerferon production regulator |
| GDB: 134207 | 9p22 | 9p22 | | IFNW1 |
| | | | | Hs.73010 |
| | | | | interferon, omega 1 |
| GDB: 136371 | 9p22 | 9p22 | | IFNWP15 |
| | | | | interferon, omega 15 (pseudogene) |
| GDB: 136372 | 9p22 | 9p22 | | IFNWP18 |
| | | | | interferon, omega 18 (pseudogene) |
| GDB: 136373 | 9p22 | 9p22 | | IFNWP19 |
| | | | | interferon, omega 19 (pseudogene) |
| GDB: 136374 | | | | IFNWP2 |
| | | | | interferon, omega 2 (pseudogene) |
| GDB: 136375 | | | | IFNWP4 |
| | | | | interferon, omega 4 (pseudogene) |
| GDB: 136376 | | | | IFNWP5 |
| | | | | interferon, omega 5 (pseudogene) |
| GDB: 136377 | 9p22 | 9p22 | | IFNWP9 |
| | | | | interferon, omega 9 (pseudogene) |
| GDB: 120748 | 7p21 | 7p15 | 0.6606 | IL6 |
| | 7p21 | 7p21 | | interleukin 6 (interferon, beta 2) |
| | | | | Hs.93913 |
| | | | | IFNB2 |

Experimental Protocol

Bombardment and selection of transgenic plants: Sterile *Nicotiana tabacum* cv. Petit Havana and LAMD-609 tobacco leaves were bombarded using the Bio-Rad PDS-1000/He biolistic device. The two varieties of bombarded leaves were placed on RMOP medium containing 500 μg/ml and 300 μg/ml spectinomycin, respectively, for two rounds of selection on plates. Subsequently, both tobacco varieties were moved to jars of MSO medium containing 500 μg/ml spectinomycin.

PCR analysis to test stable integration: DNA was extracted from tobacco leaves using Qiagen DNeasy Plant Mini Kit (Qiagen, Valencia, Calif.). PCR was performed using the Perkin Elmer Gene Amp PCR System 2400 (Perkin Elmer, Chicago, Ill.). PCR reactions contained template DNA, 1×Taq buffer, 0.5 mM dNTPs, 0.2 mM 3P primer, 0.2 mM 3M primer, 0.05 units/μl Taq Polymerase, and 0.5 mM $MgCl_2$. Samples were run for 30 cycles as follows: 95° C. for 1 min, 65° C. for 1 min, and 72° C. for 2 min with a 5 min ramp up at 95° C. and a 72° C. hold for 10 min after cycles complete. PCR products were separated on 1% agarose gels.

Southern blot analysis: Total plant DNA was digested with BamHI and run on a 0.8% agarose gel at 60 V for 3.5 hours. The gel was soaked in 0.25 N HCl for 15 minutes and then rinsed 2× with water. The gel was soaked in transfer buffer (0.4 N NaOH, 1 M NaCl) for 20 minutes and then transferred overnight to a nitrocellulose membrane. The membrane was rinsed twice in 2×SSC (0.3 M NaCl, 0.03 M Sodium citrate), dried on filter paper, and then crosslinked in the GS GeneLinker (Stratagene, La Jolla, Calif.). The flanking sequence probe was made by digesting pUC-CT vector DNA[13] with Ramm and BglII to generate a 0.81 kb probe. The gene specific probe was made by digesting IFNα2b with EcoRI to generate a 0.75 kb probe. The probes were labeled with $^{32}P$ using the ProbeQuant G-50 Micro Columns (Arnersham, Arlington Heights, Ill.). The probes were hybridized with the membranes using Stratagene QUICK-HYB hybridization solution and protocol (Stratagene, La Jolla, Calif.).

Western blot analysis: Approximately 100 mg of leaf tissue was ground in liquid nitrogen with a mortar and pestle and stored at −80° C. For extraction of proteins, the transgenic leaves were thawed on ice and 200 μl of plant extraction buffer was added and mixed with mechanical pestle (0.1% SDS, 100 mM NaCl, 200 mM Iris-HCl pH 8.0, 0.05% Tween 20, 400 mM sucrose, 2 mM PMSF). The plant extract was then centrifuged for 5 minutes at 10,000×g to pellet the plant material. The supernatant containing the extracted protein was transferred to a fresh tube and an aliquot was taken out, combined with sample loading buffer, boiled, and then run on 15% SDS-PAGE gels for one hour at 80 V, then 3.5 hours at 150 V. Gels were transferred overnight at 10 V to nitrocellulose membrane. The membrane was blocked with PTM (1×PBS, 0.05% Tween 20, and 3% dry milk). IFNα2b was detected with Mouse Anti-Human Interferon α monoclonal antibody. Secondary antibody used was goat anti-mouse IgG conjugated to horseradish peroxidase (American Qualex Antibodies, A106PN). The interferon standard was PEG-Intron™, which had a molecular weight of 32 kDa because polyethylene glycol (PEG) is attached to the IFNα2b to increase the drug's half-life in the bloodstream.

All references contained herein, and listed in the reference section are fully incorporated by reference into this application.

REFERENCES

1. Abkevich, V., Shakhnovich, E. (2000). "What can Disulfide bonds tell us about Protein Energetics, Function, and Folding: Simulations and Bioinformatics Analysis". *J. Mol. Biol.* 300, 975-985.
2. Arakawa, T., Yu, J., Chong, D. K. X. et al. (1997). "Expression of Cholera toxin B subunit oligomers in transgenic potato plants". *Transgenic Research,* 6, 403-413.
3. Baron, S., Tyring, S., Fleischmann, W., Coppenhaver, D., Niesel, D., Klimpel, G., Staton, G., Huges, T. (1991). "The interferons: mechanism of action and clinical applications." *J. Amer. Med. Assoc.,* 266, 1375-1383.
4. Baron, S., Coppenhaver, D., Dianzani, F., Fleischmann, W., Hughes, T., Klimpel, G., Niesel, D., Stanton, G., Tyring, S. (1992). *Interferon: principles and medical applications*. Baron, 1-15.
5. Bendich, A. (1987). "Why do chloroplasts and mitochondria contain so many copies of their genome?" *BioEssays.* 6, 279-282.
6. Bhojwani, S. (1990). *Plant Tissue Culture: Applications and Limitations*. Elsevier, Amsterdam.
7. Bock, R., Hagemann, R. (2000). "Extranuclear Inheritance: Plastid Genetics: Manipulation of Plastid Genomes and Biotechnological Applications." *Genetics*. Springer-Verlag Berlin Heidelberg.
8. Bogorad, L. (2000). "Engineering chloroplasts: an alternative site for foreign gene, proteins, reactions and products." *TIBTECH,* 18, 257-263.
9. Bovolenta, C., Driggers, P., Marks, M., Medin, J., Politis, A., Voge; S., Levy, D., Sakaguchi, E., Coligan, J., Ozato, K. (1994). "Molecular interactions between interferon consensus binding protein and members of the interferon regulatory factor family." *Proc. Natl. Acad. Sci. USA.* 91, 5046-5050.
10. Bradford, M. (1976). "A rapid and sensitive method for the quantification of microgram quantities of protein utilizing the principle of protein-dye binding." *Anal. Biochem.* 72, 248-254.
11. Braun, A., Kwee, L., Labow, M., Alsenz, J. (1997). "Protein aggregates seem to play a key role among the parameters influenceing the antigenicity of interferon alpha (IFN-alpha) in normal and transgenic mice." *Pharm. Res.* 14(10), 1472-1478.
12. Brixey, M., Guda, C., Daniell, H., (1997) "The chloroplast psbA promoter is more efficient in *E. coli* than the T7 promoter for hyper-expression of a foreign protein." *Biotechnology Letters.* 19, 395-400
13. Bruick, R., Mayfield, S. (1999). "Light-activated translation of chloroplast mRNA." *Trends Plant Sci.* 4, 190-195.
14. Carlson, P. S. (1973). "The use of protoplasts for genetic research." *Proc. Natl. Acad. Sci. USA,* 70, 598-602.
15. Castelruiz, Y., Larrea, E., Boua, P., Civeira, M., Prieto, J. (1999). *Hepatology* 1900-1904.
16. Centers for Disease Control and Prevention., Atlanta, Ga., USA.
17. Colamonici, O., D'Alessandro, F., Diaz, M., Gregory, S., Neckers, L., Nordan, R. (1990). "Characterization of three monoclonal antibodies that recognize the interferon α2 receptor." *Proc. Natl. Acad. Sci. USA* 87, 7230-7234.
18. Collins, Legg, Kasperbauer (1974). "Tobb'aco hybrid, LAMID-609." *Crop Sci.* 14, 77-80.
19. Cook, J., Cleary, C., Mariano, T., Izotova, L., Pestka, S. (1996). "Differential responsiveness of a splice variant of the human type I interferon receptor to interferons." *J Biol. Chem.* 271, 13448-13453.
20. Cowley, D., Mackin, R. (1996). "Expression, purification and characterization of recombinant human proinsulin." *FEBS Letters* 402, 124-130.
21. Cramer, C., Boothe, J., Oishi, K. (1999). "Transgenic Plants for Therapeutic Protein: Linking Upstream and Downstream Strategies." *Curr. Top. Microbiol. Immunol.* 240, 95-118.
22. Cross, J., Roberts, R. (1991). "Constitutive and trophoblast-specific expression of a class of bovine interferon genes." *Proc. Natl. Acad. Sci. USA.* 88, 3817-3821.
23. Crossin, K., Carney, D., (1981). "Evidence that microtubule depolymerization early in the cell cycle is sufficient to initiate DNA synthesis." *Cell* 23, 61-71.
24. Cummins, Jr.; J. (1984) "Delivery of biologically active components of hererologous species interferon isolates." U.S. Pat. No. 4,462,985.
25. Daniell, H., Rebeiz, C. A. (1982). "Chloroplast culture IX: Chlorphyll(ide) A biosynthesis in vitro at rates higher than in vivo." *Biochem. Biophys. Res. Comun.,* 106, 466-471.
26. Daniell H., Ramanujan, P., Krishnan, M., Gnanam, A., Rebeiz, C. A. (1983). "In vitro synthesis of photosynthetic membranes: I. Development of photosystem I activity and cyclic phosphorylation." *Biochem. Biophys. Res. Comun.,* 111, 740-749.
27. Daniell H., Krishnan, M., Umabai, U., Gnanam, A. (1986). "An efficient and prolonged in vitro translational system from cucumber etioplasts." *Biochem. Biophys. Res. Comun.,* 135, 48-255.
28. Daniell H., McFadden, B. A. (1987). "Uptake and expression of bacterial and cyanobacterial genes by isolated cucumber etioplasts." *Proc. Natl. Acad. Sci. USA,* 84., 6349-6353.
29. Daniell, H., McFadden, B. A. (1988). "Genetic Engineering of plant chloroplasts." U.S. Pat. Nos. 5,932,479; 5,693,507.
30. Daniell H., Vivekananda, J., Neilsen, B., Ye, G. N., Tewari, K. K., Sanford, J. C. (1990). "Transient foreign gene expression in chloroplasts of cultured tobacco cells following biolistic delivery of chloroplast vectors." *Proc Natl Acad Sci USA.,* 87, 88-92.
31. Daniell H., Krishnan, M., McFadden, B. A. (1991). "Expression of B-glucuronidase gene in different cellular compartments following biolistic delivery of foreign DNA into wheat leaves and calli." *Plant Cell Reports,* 9, 615-619.
32. Daniell, H. (1993). "Foreign gene expression in chloroplasts of higher plants mediated by tungsten particle bombardment." *Methods Enzymol.,* 217, 536-556.
33. Daniell, H. (1997). "Transformation and foreign gene expression in plants mediated by microprojectile bombardment." *Meth Mol Biol.,* 62, 453-488.

34. Daniell, H., *Datta*, R., Varma, S., Gray, S., & Lee, S. B. (1998). "Containment of herbicide resistance through genetic engineering of the chloroplast genome." *Nature Biotechnology,* 16, 345-348.
35. Daniell, H. (1999). "Universal chloroplast integration and expression vectors, transformed plants and products thereof, World Intellectual Property Organization." WO 99/10513.
36. Daniell, H., Streafield, S. J., & Wycoff, K. (2001a). "Medical molecular farming: production of antibodies, biopharmaceuticals and edible vaccines in plants." *Trends Plant Sci.,* 6(5), 219-26.
37. Daniell, H., Lee, S. B., Panchal, T., Wiebe, P. O. (2001b). "Expression of the native cholera toxin B subunit gene and assembly of functional oligomers in transgenic tobacco chloroplasts." *Journal of Molecular Biology,* 311, 1001-1009.
38. Daniell, H., Muthukumar, B., Lee, S. B. (2001c). "Marker free transgenic plants: engineering the chloroplast genome without the use of antibiotic selection." *Curr Genet.,* 39(2), 109-16.
39. Daniell, H., Khan, M. S., & Allison, L. (2002). "Milestones in chloroplast genetic engineering: an environmentally friendly era in biotechnology." *Trends in Plant Science,* 7, 84-91.
40. Daniell, H.,& Dhingra, A. (2002). "Multiple gene engineering." *Current Opinion in Biotechnology,* 13, 136-141.
41. Daniell, H. (2002). "Molecular strategies for gene containment in GM crops." *Nature Biotechnology,* 20, 581-586.
42. Danon, A. (1997). "Translational regulation in the chloroplast." *Plant Physiol.* 115, 1293-1298.
43. De Cosa, B., Moar, W., Lee, S. B., Miller, M.,& Daniell, H. (2001). "Hyper-expression of Bt Cry2Aa2 operon in chloroplasts leads to formation of insecticidal crystals." *Nature Biotechnology,* 19, 71-74.
44. DeGray, G., Rajasekaran, K., Smith, F., Sanford, J., Daniell, H. (2001). "Expression of an antimicrobial peptide via the chloroplast genome to control phytopathogenic bacteria and fungi." *Plant Physiology,* 127, 1-11.
45. De Maeyer, E., De Maeyer-Guignard, J. (1988). "Interferons and other Regulatory Cytokines." *Wiley*, New York, 380-424.
46. Der, S., Lau, A. (1995). "Involvement of the double-stranded-RNA-dependent kinase PKR in interferon expression and interferon-mediated antiviral activity." *Proc. Natl. Acad. Sci. USA* 92, 8841-8845.
47. Dianzani, F., Baron, S. (1975). "Unexpectedly rapid action of human interferon in physiological conditions." *Nature,* 257, 682-684.
48. Dimmock, N., Primose, S. (1994). "The Immune System and Interferon." *Introduction to modern Virology*. Fourth Edition. 205-213.
49. Edwards, K., Johnstone, C., & Thompson, C. (1991). "A simple and rapid method for preparation of plant genomic DNA for PCR analysis." *Nucleic Acid Res.,* 19, 1349.
50. Eibl, C., Zou, Z., Beck, A., Kim, M., Mullet, S., Koop, H. (1999). "In vivo analysis of plastid psbA, rbcL and rpl32UTR elements by chloroplast transformation: tobacco plastid gene expression is controlled by modulation of transcript levels, and translational efficiency." *Plant J.* 19, 333-345
51. Elderbaum, O., Stein, D., Holland, N., Gafni, Y., Livneh, O., Novick, D., Rubinstein, M., Sele, I. (1992). "Expression of active human interferon beta in transgenic plants." *J. Interferon Research.* 12, 449-453.
52. Ferbas, J., Toso, J., Logar A., Navratil, J., Rinaldo, C., (1994). "CD4+ blood dendritic cells are potent producers of IFN-α in response to in vitro HIV-1 infection." *J. Immunol.,* 152, 4649-4662.
53. Fernández-San Millán, A., Mingo-Castel, A., Daniell, H. (2003). "A chloroplast transgenic approach to hyper-express and purify human serum albumin, a protein highly susceptible to proteolytic degradation." *Plant Biotechnology Journal*, in press.
54. Fitzgerald-Bocarsly, P. (1993). "Human natural interferon-α producing cells." *Pharmacol. Ther.,* 60, 39-62
55. Gerace, L., (1985): Structural proteins in the eukaryotic nucleus." *Nature* 318, 508-509.
56. Giddings, G., Allison, G., Brooks, D., Carter, A. (2000). "Transgenic plants as factories for biopharmaceuticals." *Nature Biotechnology* 18, 1151-1155
57. Glick, B., Pasternak, J. (1998). *Molecular Biotechnology: Principles and Applications of Recombinant DNA*. ASM Press, $2^{nd}$ edition.
58. Gomez-Orellana, I., Paton, D. (1998). "Advances in the Oral Delivery of Proteins." Exp. Opin. Ther. Patents 8(3), 223-234.
59. Guda, C., Lee, S. B., & Daniell, H. (2000). "Stable expression of biodegradable protein based polymer in tobacco chloroplasts." *Plant Cell Rep.,* 19, 257-262.
60. Gutterman, J. (1994). "Cytokine therapeutics: Lessons from interferon α." *Proc. Natl. Acad. Sci. USA,* 91, 1198-1205
61. Gwynne, D., Buxton, F., Pickett, M., Davies, R., Scazzocchio, C. (1993). "Vectors in use in filamentous fungi." U.S. Pat. No. 5,198,345.
62. Haq, T. A., Mason, H. S., Clements, J. D., Arntzen, C. J. (1995). "Oral immunization with a recombinant bacterial antigen produced in transgenic plants." *Science,* 268, 714-716.
63. Hager, M., Bock, R. (2000). "Enslaved bacteria as new hope for plant biotechnologist." *Appl. Microbiology Biotechnol.* 54, 302-310.
64. Harris-Stuart, R., Penny, R. (1997). *Clinical Applications of the Interferons*. Chapman & Hall Medical.
65. Hajdukiewicz, P., Allison, L., Maliga, P. (1996). "The two RNA polymerases encoded by the nuclear and the plastid compartments transcribe distinct groups of genes in tobacco plastids." *The EMBO Journal* 16, 4041-4048.
66. Heath, D., Anderson, G., Maurot, M., Welkos, S., Andrews, G., Adamovicz, J., Friedlander, A. (1998). "Protection against experimental bubonic and pneumonic plague by a recombinant capsular F1-V antigen fusion protein vaccine." *Vaccine,* 16, 1131-1137.
67. Heifetz, P., Tuttle, A. (2001) "Protein expression in plastids." *Current Opinion in Plant Biology* 4, 157-161.
68. Henco, K., Brosius, S., Fujisawa, A. (1985). "Structural relationship of human interferon alpha genes and pseudogenes." *J. Mol Biol.* 185, 227-260.
69. Invitrogen Catalog, 2000.
70. Isaacs, A., Lindenmann J., (1957). "Virus interference. I. The interferon. *Proc R Soc. Ser. B* 147, 258-267.
71. Kavanagh, T., Thank N., Lao, N., McGrath, N., Peter, S., Horvath, E., Dix, P., Medgyest, P. (1999). "Homeologous Plastid DNA Transformation in Tobacco is Mediated by Multiple Recombination Events." *Genetics,* 152, 1111-1122.
72. Kim, J., Mayfield, S. (1997). "Protein Disulfide Isomerase as a Regulator of Chloroplast Translational Activation." *Science* 278, 1954-1957.
73. Kong Q., Richter, L., Yang, Y., Arntzen, C., Mason, H., Thanavala, Y. (2001). "Oral immunization with hepatitis B surface antigen expressed in transgenic plants." *Proc. Natl. Acad. Sci. USA,* 98, 20, 11539-11544.

74. Kuby, J (1997). *Immunology*, W.H. Freeman and Company, third edition.

75. Kusnadi, A., Nikolov, Z., & Howard, J. (1997). "Production of Recombinant proteins in Transgenic plants: Practical considerations." *Biotechnology and Bioengineering,* 56 (5), 473-484.

76. Laemmli, U. (1970). "Cleavage of structural proteins during the assembly of the head of bacteriophage T4." *Nature,* 227; 680-685

77. Lampson, G., Tytell, A., Field, A., (1967). "Inducers of interferon and host resistance. I. Double-stranded RNA from extracts of *Penicillium funiculosum" Proc. Natl. Acad. Sci. USA.,* 58, 782-789.

78. Larrea, E., Alberdi, A., Castelruiz, Y., Boya, P., Civeira, M., Prieto, J. (2001) *Journal of Viral Hepatitis* 8, 1-7.

79. Lee, S. B., Kwon, H., Kwon, S., Park, S., Jeong, M., Han, S., Daniell, H., Byun, H. (2001). "Drought tolerance conferred by the yeast trehalose-6 phosphate synthase gene engineered via the chloroplast genome." *Transgenic Research. In press.*

80. Lencer, W. I., Moe, S., Rufo, P. A. & Madara, J. L. (1995). "Transcytosis of cholera toxin subunits across model human intestinal epithelia." *Proc. Natl. Acad Sci USA.,* 92, 10094-10098.

81. Lindenmann, J., Schleuning, W. (1999). *Interferon: The Dawn of Recombinant Protein Drugs*. Springer.

82. Macieira-Coelho, A. (1990). *Cancer and aging at the cellular level.* CRC Press, Boca Rotan, 11-37.

83. Macieira-Coelho, A. (1998) *Inhibitors of cell Growth.* "Progress in Molecular and Subcellular Biology." Springer.

84. Maeda, S., Kawai, T., Obinata, M., Fujiwara, H., Horiuchi, T., Sacki, Y., Sato, Y., Furusawa, M. (1985). "Production of human alpha-interferon in silkworm using a baculovirus vector." *Nature* 13-19; 315 96020): 592-4.

85. Malta, P. (1993). "Towards plastid transformation in flowering plants." *TIBTECH.* 11, 101-106.

86. Murashige, T., Skoog, F. (1962). "A revised medium for rapid growth and bioassays with tobacco tissue culture." *Physiol. Plant* 15, 473-497

87. Martin, W., Herrmann, R., (1998). "Gene Transfer from Organelles to the Nucleus: How Much, What Happens, and Why?" *Plant Physiol.* 118, 9-17.

88. Mason, H., Lam, M., Arntzen, C. (1992). "Expression of hepatitis B surface antigen in transgenic plants." *Proc. Natl. Acad. Sci. USA.* 89, 11745-11749.

89. Mathiowitz, E., Jacob, J. S., Jong, Y. S., Carino, G. P., Chickering, D. E., Chaturvedi, P., Santos, C. A., Vijayarahauau, K., Montgomery, S., Bassett, M., & Morrell, C. (1997). "Biologically erodable microspheres as potential oral drug delivery systems." *Nature,* 386, 410-414.

90. May, G. D., Mason, H. S., & Lyons, P. C. (1996). "Application of transgenic plants as production systems for pharmaceuticals in ACS symposium series 647." Fuller et al. eds., chapter 13, 196-204.

91. McBride, K. E., Svab, Z., Schaaf, D. J., Hogen, P. S., Stalker, D. M., & Maliga, P. (1995). Amplification of a chimeric *Bacillus* gene in chloroplasts leads to extraordinary level of an insecticidal protein in tobacco. *Biotechnology,* 13, 362-365.

92. Moriya, O., Matsui, M., Osorio, M., Miyazawa, H., et al (2002). "Induction of hepatitis C virus-specific cytotoxic T lymphocytes in mice by immunization with dendritic cells treated with an anthrax toxin fusion protein." *Vaccine.,* 20, 789-796.

93. Muller, U., Steinhoff, U., Reis, L., Hemmi, S., Pavlovic, J., Zinkernagel, R., Auguet, M. (1994). "Functional role of type I and type II interferons in antiviral defense." *Science.* 264, 1918-1921.

94. New England Biolabs Catalog (2000-2001).

95. Nygren, P., Stahl, S., Uhien, M. (1994). "Engineering proteins to facilitate bioprocessing." *TIBTECH* 12, 184-186.

96. Ohya, K., Matsumura, T., Ohashi, K., Onuma, M., Sugimoto, C. (2001). "Expression of two subtypes of human IFN-alpha in transgenic potato plants." *Journal of Interferon and Cytokine Research.* 21(8), 595-602.

97. Pestka, S., Langer, J., Zoon, K., Samuel, C. (1987). "Interferons and their actions." *Annu Rev. Biochem,* 56.727-777.

98. Petridis, D., Sapidou, E. & Calandranis, J. (1995). "Computer-Aided process analysis and economic evaluation of for biosynthetic human insulin production." A case study. *Biotechnology and Bioengineering,* 48, 529-541.

99. Purvis, I. J., Bettany, A. J., Santiago, T. C., Coggins, J. R., et al (1987). "The efficiency of folding of some proteins is increased by controlled rates of translation in vivo." *J. Mol. Biol.,* 193, 413-417.

100. Rathinasabapathy, B. (1994). "Metabolic engineering of glycine betaine synthesis: plant betaine aldehyde dehydrogenase lacking typical transit peptides are targeted to tobacco chloroplasts where they confer aldehyde resistance." *Planta* 193, 155-162.

101. Reichert, J. (2000). "New biopharmaceuticals in the USA: trends in development and marketing approvals 1995-1999." *TITECH,* 18: 364-369.

102. Ruelland, E., Miginiac-Maslow, M. (1999). "Regulation of chloroplast enzyme activities by thioredoxins: activation or relief form inhibition?" *Trends Plant Sci.* 4, 136-141.

103. Rubinstein, M., Orchansky, P. (1986). "The interferon receptors." *CRC Crit.* Rev. Biochem. 21, 249-277.

104. Ruf, S., Hermann, M., Berger, Carer, H., & Bock, R. (2001). "Stable genetic transformation of tomato plastids: high level foreign protein expression in fruits." *Nature Biotechnology,* 19, 870-875.

105. Sambrook, J., Fritsch, E., Maniatis, T. (1989) "Molecular Cloning; A Laboratory Manual." *Cold Spring Harbor Laboratory Press, 2nd edition.*

106. Sanford, J. C., Smith, F. D., Russell, J. A. (1993). "Optimizing the Biolistic Process for Different Biological Applications." *Methods in Enzymology,* 217, 483-509.

107. Sidorov, V. A., Kasten, D., Pang, S. Z., Hajdukiewicz, P. T. J., Staub, J. M., Nehra, N. S. (1999). "Stable chloroplast transformation in potato: use of green fluorescent protein as a plastid marker." *Plant Journal,* 19, 209-216.

108. Slocombe, P., Easton, A., Boseley, P., Burke, D. (1982). "High-level expression of an interferon $\alpha 2$ gene cloned in phage M13mp7 and subsequent purification with a monoclonal antibody." *Proc. Natl. Acad. Sci. USA.* 79, 5455-5459.

109. Staub, J., Maliga, P. (1993). "Accumulation of D1 polypeptide in tobacco plastids is regulated via the untranslated region of the psbA mRNA." *The EMBO Journal* 12, 601-606.

110. Staub, J., Garcia, B., Graves, J., Hajdukiewicz, et al (2000). "High yield production of human therapeutic protein in tobacco chloroplasts." *Nat Biotechnol.,* 18, 333-338.

111. Svab, Z., Maliga, P. (1993). "High frequency plastid transformation in tobacco by selection for a chimeric aadA gene." *Proc. Natl. Acad. Sci. USA.,* 90, 913-917.
112. Swaminathan, S., Khanna, N., (1999). "Affinity purification of recombinant interferon alpha on a mimetic ligand adsorbent." Protein Expre Purif. 5, 236-242.
113. Thatcher, D R., Panayotatos, N. (1986) "Related Purification of recombinant human IFN-α2. Methods Enzymol." 119, 166-177.
114. Tompkins, W. (1999). "Immunomodulation and therapeutic effects of the oral use of interferon-alpha: mechanism of action." *Journal of interferon and cytokine research.* 19, (8) 817-828.
115. Torres, M. (2001) "Expression of Interferon α5 in transgenic tobacco chloroplasts." *Masters Thesis, University of Central Florida.*
116. Trinchieri, G., Santoli, D., Granato, D., Perussia, B. (1981). "Antagonistic effects of interferons on the cytotoxicity mediated by natural killer cells." *Fed. Proc.,* 40, 2705-2710.
117. Walmsley, A., & Arntzen, C. (2000). "Plants for Delivery of Edible Vaccines." *Current Opinion in Biotechnology,* 11, 126-129.
118. Walsh, G. (1998). "Biopharmaceuticals:" *Biochemistry and Biotechnology.* Wiley.
119. Walsh, G. (2000). "Biopharmaceutical benchmarks." *Nature Biotechnology.* 18, 831-832.
120. Watson, J., Hopkins, N., Roberts, J., Stefitz, J., Weiner, A. (1987). *Molecular Biology of the Gene.* Benjamin/Cummings, fourth edition, 945-949.
121. Weiss K. (1998). "Safety Profile of Interferon-α Therapy." *Seminars in Oncology,* 25, 9-13.
122. Wilson, V., Jeffreys, A., Bathe, P., Boseley, P., Slocombe, P., Easton, A., Burke, D., (1983). "A comparison of vertebrate interferon gene families detected by hybridization with human interferon DNA." *J. Mol. Biol.* 166, 457-475.
123. World Health Orgsnization(1998). World Health Report
124. Ye, G. N., Daniell, H., & Sanford, J. C. (1990). "Optimization of delivery of foreign DNA into higher-plant chloroplasts." *Plant Mol. Biol.,* 15 (6), 809-819.
125. Yu, J., & Langridge, H. R. (2001). "A plant-based multicomponent vaccine protects mice from enteric diseases." *Nat. Biotech.,* 19, 548-552.
126. Zerges, W. (2000). "Translation in chloroplasts." *Biochimie* 82, 583-601.
127. Zoon, W., Okuno, T. (1987). "Interferon receptors." *The Interferon System: A current review to* 1987.
128. Zhou, M., Gomez-Sanchez, C. (2000). "Universal TA cloning." *Curr. Issues Mol. Biol,* 2(1), 1-7.
129. Zhu, Z., Huges, K., Huang, L. (1994). "Expression of human alpha-interferon cDNA in transgenic rice." Plant Cell Tiss. Org. Cult. 26, 197-204.

The invention claimed is:

1. A plastid transformation vector for stably transforming a target plastid genome, said vector comprising, as operably-linked components, a flanking sequence homologous to a trnI region in the plastid genome, a construct comprising a regulatory sequence comprising a 16S rRNA promoter operative in a plastid genome operably-linked to a light regulated psbA 5' untranslated region element operably-linked to a DNA sequence coding for an IFNα2b polypeptide operably-linked to a psbA 3' untranslated region element, and a flanking sequence homologous to a trnA region in the plastid genome, wherein said flanking sequences stably integrate the construct into an inverted repeat region of the target plastid genome through homologous recombination, and wherein said vector further comprises DNA sequence encoding a betaine aldehyde dehydrogenase (BADH) selectable marker.

2. The vector of claim 1, wherein said IFNα2b polypeptide further comprises a polyhistidine purification tag and a thrombin cleavage site.

3. A method for producing IFNα2b, said method comprising: integrating the plastid transformation vector of claim 1 into the plastid genome of a plant cell; and growing said plant cell to thereby express said IFNα2b, wherein said IFNα2b polypeptide is competent to produce an immunogenic response in a mammalian cell.

4. The method of claim 3, further comprising: extracting said IFNα2b from leaves of said plant and isolating said IFNα2b polypeptide from other plant proteins.

5. A homoplasmic plant stably transformed with the transformation vector of claim 1, wherein the plant produces IFNα2b, and wherein the IFNα2b polypeptide is competent to induce an immunogenic response in a mammal.

6. A transplastomic progeny or seed of the plant of claim 5, wherein the progeny or seed comprises the construct and selectable marker.

7. The plant of claim 5, wherein said plant is an edible plant suitable for mammal consumption.

8. The plant of claim 7, wherein said edible plant is LAMD-609.

9. The plant of claim 5, wherein the expression of said IFNα2b polypeptide is at least about 6.0 percent total soluble protein.

* * * * *